US011679260B2

(12) United States Patent
Senderowicz et al.

(10) Patent No.: US 11,679,260 B2
(45) Date of Patent: *Jun. 20, 2023

(54) APPARATUS FOR TREATING NEUROLOGICAL DISORDERS BY ELECTROSTIMULATION AND METHOD FOR PROCESSING NEURAL SIGNALS COLLECTED BY THE SAID APPARATUS

(71) Applicant: Newronika S.p.A., Milan (IT)

(72) Inventors: Daniel Senderowicz, Berkeley, CA (US); Mattia Arlotti, Rimini (IT); Nicolo Vieno, Campodarsego (IT); Lorenzo Rossi, Trento (IT)

(73) Assignee: Newronika S.p.A., Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 17/165,124

(22) Filed: Feb. 2, 2021

(65) Prior Publication Data

US 2021/0154476 A1    May 27, 2021

Related U.S. Application Data

(63) Continuation of application No. 16/282,167, filed on Feb. 21, 2019, now Pat. No. 10,933,243.

(30) Foreign Application Priority Data

Feb. 22, 2018  (IT) .................. 102018000002962

(51) Int. Cl.
*A61N 1/36* (2006.01)
*A61N 1/05* (2006.01)
(Continued)

(52) U.S. Cl.
CPC ........ *A61N 1/36067* (2013.01); *A61B 5/0006* (2013.01); *A61B 5/30* (2021.01);
(Continued)

(58) Field of Classification Search
CPC ...... A61N 1/0534; A61N 1/16; A61N 1/3605; A61N 1/36067; A61N 1/36125;
(Continued)

(56) References Cited

U.S. PATENT DOCUMENTS 5,683,422 A    11/1997 Rise
6,360,122 B1    3/2002 Fischell et al.
(Continued)

FOREIGN PATENT DOCUMENTS

EP     2 004 036 B1    7/2011
EP     1 940 508 B1    12/2011
(Continued)

OTHER PUBLICATIONS

BioWorld MedTech (2019). Cortera WAND Technology, Clarivate Analytics, 10 total pages.
(Continued)

*Primary Examiner* — Carl H Layno
*Assistant Examiner* — Anh-Khoa N Dinh
(74) *Attorney, Agent, or Firm* — Cooley LLP

(57) ABSTRACT

The present disclosure relates to apparatuses and methods for treating neurological disorders by electro-stimulation. In some embodiments, the apparatus includes a stimulation module configured to generate a stimulation signal to be sent to at least one implantable electrode, and an acquisition module configured to acquire a signal measured by the at least one implantable electrode from a patient. The acquisition module may include a front-end block configured to amplify a potential difference of input signals ($V_1a$, $V_2a$) received by the acquisition module and to filter a stimulus artifact by cutting off frequencies above a predefined frequency band. The front-end block may include a multi-stage fully-differential switched capacitor circuit configured for discrete-time signal processing.

34 Claims, 10 Drawing Sheets

(51) Int. Cl.
*A61N 1/16* (2006.01)
*A61B 5/00* (2006.01)
*A61B 5/30* (2021.01)
*A61B 5/316* (2021.01)

(52) U.S. Cl.
CPC ............ *A61B 5/316* (2021.01); *A61N 1/0534* (2013.01); *A61N 1/16* (2013.01); *A61N 1/3605* (2013.01); *A61N 1/36125* (2013.01); *A61N 1/36135* (2013.01)

(58) Field of Classification Search
CPC ............ A61N 1/36135; A61N 1/36114; A61N 1/36117; A61N 1/36062; A61N 1/36071; A61N 1/36189; A61N 1/36192; A61N 1/36196; A61N 1/36146; A61N 1/3615; A61N 1/36167; A61N 1/36182; A61B 5/0006; A61B 5/30; A61B 5/316; A61B 5/0002; A61B 2560/0209; A61B 5/7203; A61B 5/7228; A61B 5/103; A61B 5/053; A61B 5/08; A61B 5/11
See application file for complete search history.

(56) References Cited

U.S. PATENT DOCUMENTS

| | | |
|---|---|---|
| 6,366,813 B1 | 4/2002 | DiLorenzo |
| 6,473,639 B1 | 10/2002 | Fischell et al. |
| 6,480,743 B1 | 11/2002 | Kirkpatrick et al. |
| 6,820,019 B1 | 11/2004 | Kelly et al. |
| 6,873,872 B2 | 3/2005 | Gkuckman et al. |
| 6,993,384 B2 | 1/2006 | Bradley et al. |
| 7,024,247 B2 | 4/2006 | Gliner et al. |
| 7,089,059 B1 | 8/2006 | Pless |
| 7,127,296 B2 | 10/2006 | Bradley |
| 7,177,678 B1 | 2/2007 | Osorio et al. |
| 7,231,254 B2 | 6/2007 | DiLorenzo |
| 7,236,830 B2 | 6/2007 | Gliner |
| 7,277,758 B2 | 10/2007 | DiLorenzo |
| 7,385,443 B1 | 6/2008 | Denison |
| 7,620,456 B2 | 11/2009 | Gliner et al. |
| 7,787,958 B2 | 8/2010 | Stevenson |
| 7,847,628 B2 | 12/2010 | Denison |
| 8,019,419 B1 | 9/2011 | Panescu et al. |
| 8,078,281 B2 | 12/2011 | Priori et al. |
| 8,135,473 B2 | 3/2012 | Miesel et al. |
| 8,190,251 B2 | 5/2012 | Molnar et al. |
| 8,224,452 B2 | 7/2012 | Pless et al. |
| 8,280,514 B2 | 10/2012 | Lozano et al. |
| 8,354,881 B2 | 1/2013 | Denison et al. |
| 8,396,565 B2 | 3/2013 | Singhal et al. |
| 8,423,145 B2 | 4/2013 | Pless et al. |
| 8,473,063 B2 | 6/2013 | Gupta et al. |
| 8,504,154 B2 | 8/2013 | Wanasek |
| 8,521,294 B2 | 8/2013 | Sarma et al. |
| 8,543,221 B2 | 9/2013 | Campbell et al. |
| 8,594,795 B2 | 11/2013 | Tcheng et al. |
| 8,644,930 B2 | 2/2014 | Kelly |
| 8,679,038 B1 | 3/2014 | Giuffrida |
| 8,718,757 B2 | 5/2014 | Bradley et al. |
| 8,744,587 B2 | 6/2014 | Miesel et al. |
| 8,825,175 B2 | 9/2014 | King |
| 8,892,208 B2 | 11/2014 | Flynn et al. |
| 8,942,809 B2 | 1/2015 | Assaf et al. |
| 8,954,152 B2 | 2/2015 | Gupta et al. |
| 8,983,617 B2 | 3/2015 | Chavan et al. |
| 9,002,449 B2 | 4/2015 | Kameli |
| 9,061,140 B2 | 6/2015 | Shi et al. |
| 9,089,704 B2 | 7/2015 | Kelly |
| 9,119,964 B2 | 9/2015 | Marnfeldt |
| 9,192,760 B2 | 11/2015 | Bradley et al. |
| 9,211,417 B2 | 12/2015 | Heldman et al. |
| 9,238,138 B2 | 1/2016 | Lee et al. |
| 9,248,280 B2 | 2/2016 | Moffitt et al. |
| 9,375,582 B2 | 6/2016 | Kaula et al. |
| 9,381,356 B2 | 7/2016 | Parker et al. |
| 9,399,132 B2 | 7/2016 | Parramon et al. |
| 9,421,379 B2 | 8/2016 | Zhu |
| 9,445,730 B2 | 9/2016 | Snyder et al. |
| 9,504,832 B2 | 11/2016 | Libbus et al. |
| 9,521,979 B2 | 12/2016 | Stanslaski et al. |
| 9,522,278 B1 | 12/2016 | Heldman et al. |
| 9,656,089 B2 | 5/2017 | Yip et al. |
| 9,750,938 B2 | 9/2017 | Ternes et al. |
| 9,844,676 B2 | 12/2017 | Zhang et al. |
| 9,888,861 B2 | 2/2018 | Carlson et al. |
| 10,154,812 B2 | 12/2018 | Howard |
| 10,219,697 B2 | 3/2019 | Muller |
| 10,471,259 B2 | 11/2019 | Stanslaski et al. |
| 10,499,854 B2 | 12/2019 | Melman et al. |
| 10,596,379 B2 | 3/2020 | Arlotti et al. |
| 10,617,877 B2 | 4/2020 | Starke et al. |
| 10,639,480 B2 | 5/2020 | Dearden et al. |
| 10,850,104 B2 | 12/2020 | Nassif |
| 10,864,368 B2 | 12/2020 | Stanslaski et al. |
| 10,933,243 B2 | 3/2021 | Senderowicz et al. |
| 11,083,402 B2 | 8/2021 | Nelson et al. |
| 11,160,979 B1 | 11/2021 | Giuffrida et al. |
| 11,160,983 B2 | 11/2021 | Stanslaski et al. |
| 11,224,747 B2 | 1/2022 | Bouton et al. |
| 11,318,296 B2 | 5/2022 | Xiao et al. |
| 11,318,309 B2 | 5/2022 | Marceglia et al. |
| 2001/0029391 A1 | 10/2001 | Gluckman et al. |
| 2002/0177882 A1 | 11/2002 | DiLorenzo |
| 2003/0114886 A1 | 6/2003 | Gluckman et al. |
| 2004/0073273 A1 | 4/2004 | Gluckman et al. |
| 2005/0065427 A1 | 3/2005 | Magill et al. |
| 2007/0162086 A1 | 7/2007 | DiLorenzo |
| 2007/0225674 A1 | 9/2007 | Molnar et al. |
| 2008/0269836 A1* | 10/2008 | Foffani ............... A61N 1/3605 607/45 |
| 2009/0099627 A1 | 4/2009 | Molnar et al. |
| 2010/0114237 A1 | 5/2010 | Giftakis et al. |
| 2010/0327887 A1 | 12/2010 | Denison et al. |
| 2016/0242645 A1 | 8/2016 | Muller |
| 2018/0085572 A1 | 3/2018 | Stanslaski et al. |
| 2018/0345019 A1 | 12/2018 | Greenberg et al. |
| 2020/0188675 A1 | 6/2020 | Marceglia et al. |
| 2020/0254261 A1 | 8/2020 | Arlotti et al. |
| 2021/0154476 A1 | 5/2021 | Senderowicz et al. |
| 2022/0323762 A1 | 10/2022 | Marceglia et al. |

FOREIGN PATENT DOCUMENTS

| | | |
|---|---|---|
| IT | 2015A000219 | 2/2016 |
| WO | WO-00/07494 A2 | 2/2000 |
| WO | WO-00/07494 A3 | 2/2000 |
| WO | WO-2007/049105 A1 | 5/2007 |
| WO | WO-2013/123112 A1 | 8/2013 |
| WO | WO-2015/069797 A1 | 5/2015 |
| WO | WO-2016/132258 A1 | 8/2016 |
| WO | WO-2018/017463 A1 | 1/2018 |
| WO | WO-2018/064193 A1 | 4/2018 |
| WO | WO-2018/064225 A1 | 4/2018 |
| WO | WO-2018/112164 A1 | 6/2018 |
| WO | WO-2018/160271 A1 | 9/2018 |
| WO | WO-2018/187080 A1 | 10/2018 |
| WO | WO-2019/073341 A1 | 4/2019 |
| WO | WO-2019/153094 A1 | 8/2019 |
| WO | WO-2020/082135 A1 | 4/2020 |
| WO | WO-2020/086119 A1 | 4/2020 |
| WO | WO-2020/087135 A1 | 5/2020 |

OTHER PUBLICATIONS

BioWorld MedTech (2018). UCSF Using Closed Loop Adaptive DBS, Clarivate Analytics, 24 total pages.

Bronstein, J.M. et al. (2011). "Deep Brain Stimulation For Parkinson Disease," Archives of Neurology 68:165-171.

Brown, P. et al. (2005). "Basal Ganglia Local Field Potential Activity: Character and Functional Significance in the Human," Clinical Neurophysiology 116:2510-2519.

(56) References Cited

OTHER PUBLICATIONS

Brown, P. et al. (2001). "Dopamine Dependency of Oscillations Between Subthalamic Nucleus and Palladium in Parkinson's Disease," J. Neurosci. 21:1033-1038.
Brown, P. (2003). "Oscillatory Nature of Human Basal Ganglia Activity; Relationship to the Pathophysiology of Parkinson's Disease," Mov. Disord. 18:357-363.
Burgess, J.G. et al. (2010). "Identifying Tremor-Related Characteristics Of Basal Ganglia Nuclei During Movement In The Parkinsonian Patient," Parkinsonism & Related Disorders 16:671-675.
Cassidy, M. et al. (2002). "Movement-Related Changes in Synchronization in the Human Basal Ganglia," Brain 125:1235-1246.
Chang, S.Y. et al. (2013). "Development Of The Mayo Investigational Neuromodulation Control System: Toward A Closed-Loop Electrochemical Feedback System For Deep Brain Stimulation," Journal of Neurosurgery 119:1556-1565.
Cogan, S.F. (2008). "Neural stimulation and recording electrodes," Annu Rev Biomed Eng. 10:275-309.
De Hemptinne, C. et al. (2015). "Therapeutic Deep Brain Stimulation Reduces Cortical Phase-Amplitude Coupling In Parkinson's Disease," Nature Neuroscience 18:779-786.
Denison, T. et al. (2007). "A 2 µW 100 nV/rtHz chopper-stabilized instrumentation amplifier for chronic measurement of neural filed potentials," IEEE J. of Solid-State Circuits 42:2934-2945.
Doyle, L.M.F. et al. (2005). "Levodopa-Induced Modulation of Subthalamic Beta Oscillations During Self-Paced Movements in Patients With Parkinson's Disease," Eur. J. Neurosci. 21:1403-1412.
Eusebio, A et al. (2011). "Deep Brain Stimulation Can Suppress Pathological Synchronisation In Parkinsonian Patients," J. of Neurol. Neurosurgery & Psychiatry 82:569-573.
Foffani, G. et al. (2003). "300-HZ Subthalamic Oscillations in Parkinson's Disease," Brain 126:2153-2163.
Foffani, G. et al. (2004). "Adaptive Autoregressive Identification with Spectral Power Decomposition for Studying Movement-Related Activity in Scalp EEG Signals and Basal Ganglia Local Field Potentials," J. Neural Eng. 1:165-173.
Foffani, G. et al. (2005). "Physiological Recordings from Electrodes Implanted in the Basal Ganglia for Deep Brain Stimulation in Parkinson's Disease. The Relevance of Fast Subthalamic Rhythms," Acta Neurochir. Suppl. 93:97-99.
Foffani, G. et al. (2005). "Altered Subthalamo-Pallidal Synchronisation in Parkinsonian Dyskinesias," J. Neural Neurosurg. Psychiatry 76:426-428.
Foffani, G. et al. (2005). "Movement-Related Frequency Modulation of Beta Oscillatory Activity in the Human Subthalamic Nucleus," J. Physiol. 568:699-711.
Fogelson, N. et al. (2005). "Reciprocal Interactions Between Oscillatory Activi-ties of Different Frequencies in the Subthalamic Region of Patients With Parkinson's Disease," Eur. J. Neurosci. 22:257-266.
Hamani, C. et al. (2005). "Bilateral subthalamic nucleus stimulation for Parkinson's disease: a systematic review of the clinical literature," Neurosurgery 56:1313-1321.
International Search Report dated May 16, 2019, for PCT Application No. PCT/IB2019/051428, filed on Feb. 21, 2019, 3 pages.
International Search Report dated May 18, 2016, for PCT Application No. PCT/IB2016/050735, filed on Feb. 11, 2016, 7 pages.
Kühn, A.A. et al. (2009). "Pathological Synchronisation In The Subthalamic Nucleus Of Patients With Parkinson's Disease Relates To Both Bradykinesia And Rigidity," Exp. Neurology 215:380-387.
Kühn, A.A. et al. (2005). "The Relationship Between Local Field Potential and Neuronal Discharge in the Subthalamic Nucleus of Patients With Parkinson's Disease," Experimental Neurology 194:212-220.
Kühn, A.A. et al. (2004). "Event-Related Beta Desynchronization in Human Subthalamic Nucleus Correlates With Motor Performance," Brain 127:735-746.

Levy, R. et al. (2002). "Dependence of Subthalamic Nucleus Oscillations on Movement and Dopamine in Parkinson's Disease," Brain 125:1196-1209.
Limousin, P. et al. (1996). "Abnormal Involuntary Movements Induced By Subthalamic Nucleus Stimulation In Parkinsonian Patients," Movement Disorders 11:231-235.
Modolo, J. et al. (2010). "Past, present and future of bran stimulation," Mathematical modelling of Natural Phenomena 5:185-207.
Modolo, J. et al. (2010). "Model-driven therapeutic treatment of neurological disorders: Reshaping brain rhythms with neuromodulation," Interface Focus 1:61-74.
Moro, E. et al. (2006). "Subthalamic Nucleus Stimulation: Improvements In Outcome With Reprogramming," Archives of Neurol. 63:1266-1272.
Notice of Allowance dated Nov. 14, 2019, for U.S. Appl. No. 15/550,284, filed Aug. 10, 2017, 7 pages.
Notice of Allowance dated Jun. 17, 2020, for U.S. Appl. No. 16/282,167, filed Feb. 21, 2019, 8 pages.
Pedram, A. et al. (2013). "A translational platform for prototyping closed-loop neuromodulation systems," Frontiers in Neural Circuits 6:117.
Priori, A et al. (2004). "Rhythm-Specific Pharmacological Modulation Of Subthalamic Activity In Parkinson's Disease," Experimental Neurology 189:369-379.
Priori, A et al. (2013). "Adaptive Deep Brain Stimulation (aDBS) Controlled by Local Field Potential Oscillations," Experimental Neurology 245:77-86.
Priori, et al, "Movement-Related Modulation of Neural Activity in Human Basal Ganglia and its L-Dopa Dependency: Recordings From Deep Brain Stimulation Electrodes in Patients With Parkinson's Disease", Neurol. Sci., Sep. 2002, pp. S101-S102.
Qian, X. et al. (2017). "A Method for Removal of Deep Brain Stimulation Artifact from Local Field Potentials," IEEE Trans. on Neural Systems and Rehabilitation Engineering, 25(12), 2217-2226.
Rosin, B. et al. (2011). "Closed-Loop Deep Brain Stimulation Is Superior in Ameliorating Parkinsonism," Neuron 72:370-384.
Santaniello, S. et al. (2011). "Closed-Loop Control of Deep Brain Stimulation: A Simulation Study," IEEE Transactions on Neural Systems and Rehabilitation Engineering 19:15-24.
Silberstein, P. et al. (2003). "Patterning of Globus Pallidus Local Field Poten-tials Differs Between Parkinson's Disease and Dystonia," Brain 126:2597-2608.
Stanslaski, S. et al. (2011). "Design and validation of a fully implantable, chronic, closed-loop neuromodulation device with concurrent sensing and stimulation," IEEE Trans Neural Syst Rehabil Eng. 20:410-421.
Williams, D. et al. (2002). "Dopamine-Dependent Changes in the Functional Connectivity Between Basal Ganglia and Cerebral Cortex in Humans," Brain 125:1558-1569.
Written Opinion of the International Searching Authority dated May 16, 2019, for PCT Application No. PCT/IB2019/051428, filed on Feb. 21, 2019, 5 pages.
Written Opinion of the International Searching Authority dated May 18, 2016, for PCT Application No. PCT/IB2016/050735, filed on Feb. 11, 2016, 8 pages.
Yoshida, F. et al. (2010). "Value Of Subthalamic Nucleus Local Field Potentials Recordings In Predicting Stimulation Parameters For Deep Brain Stimulation In Parkinson's Disease," Journal of Neurology, Neurosurgery & Psychiatry 81:885-889.
Zhao-Hui, W. et al. (2015). "Implantable analog front-end with high PSRR and CMRR for neural signal acquisition," Journal of South China University of Technology (Natural Science Edition) 43:15-20 (English Abstract Provided).
Zhou, A. et al. (2019). "A wireless and artefact-free 128-channel neuromodulation device for closed-loop stimulation and recording in non-human primates," Nature Biomedical Engin. 3:15-26.
Zhou, A. et al. (2017). WAND: A 128-channel, closed-loop, wireless artifact-free neuromodulation device, 30 total pages.
Notice of Allowance dated Dec. 17, 2021, for U.S. Appl. No. 16/706,552, filed Dec. 6, 2019, 8 pages.

(56) References Cited

OTHER PUBLICATIONS

Gui Yun et al., "A multi-channel fully differential programmable integrated circuit for neural recording application" J. Semicond. 34(10):105009-1-8 (Oct. 2013).

* cited by examiner

FIG. 4 (CONVENTIONAL INTEGRATOR)

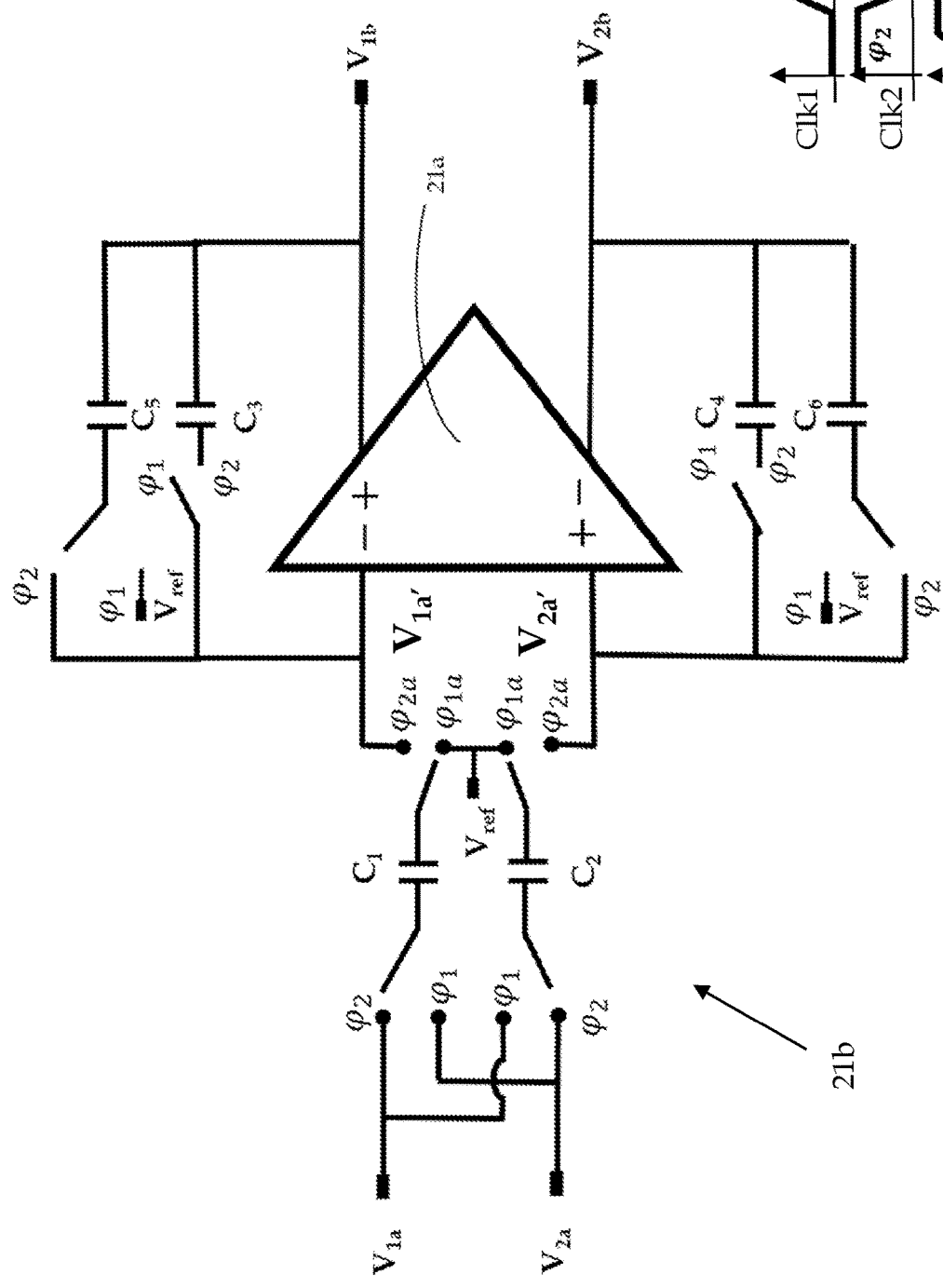
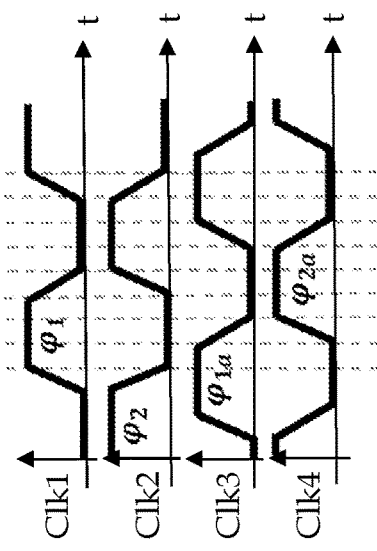
FIG. 6a
FIG. 6

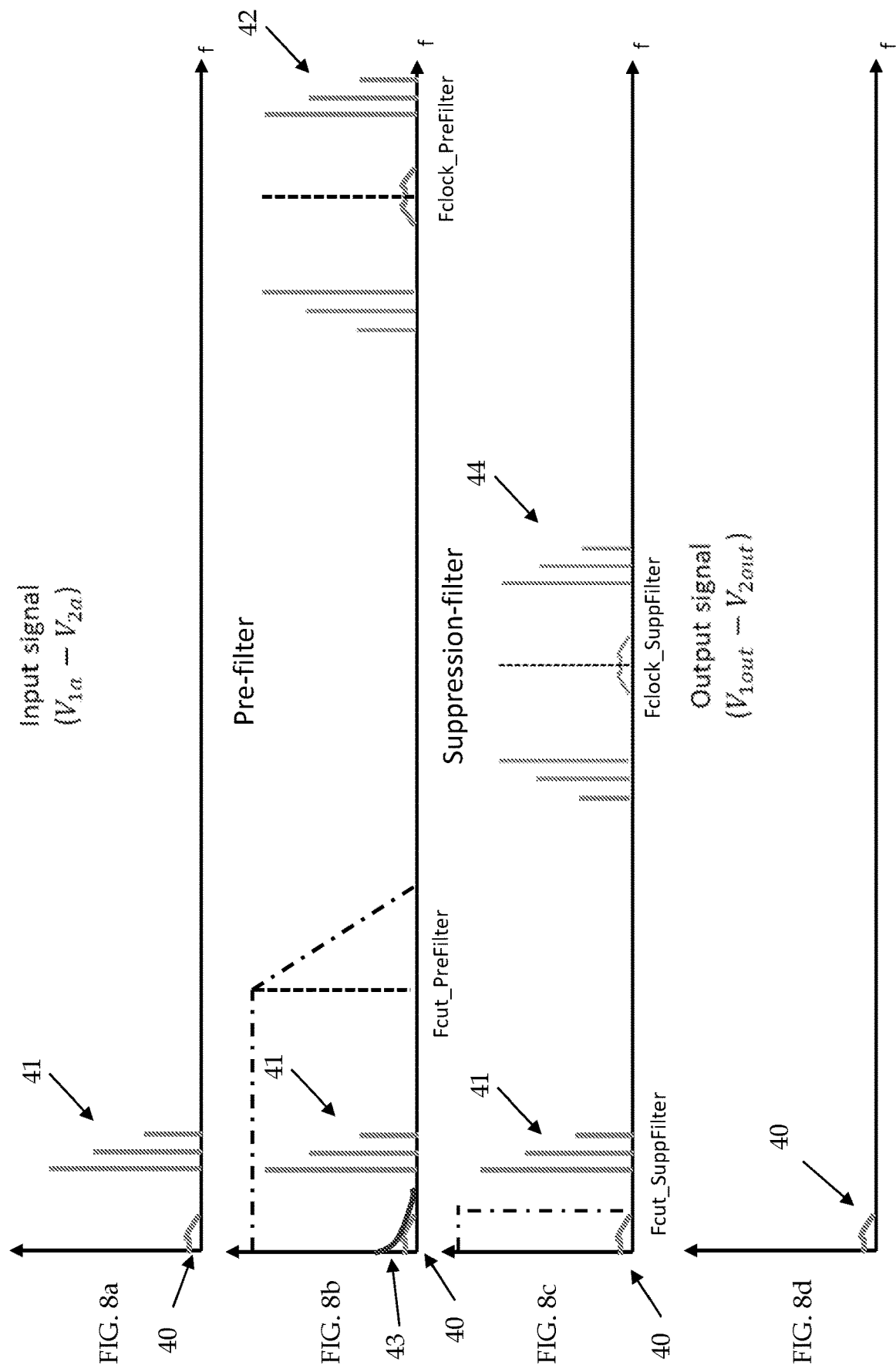

APPARATUS FOR TREATING NEUROLOGICAL DISORDERS BY ELECTROSTIMULATION AND METHOD FOR PROCESSING NEURAL SIGNALS COLLECTED BY THE SAID APPARATUS

CROSS-REFERENCE TO RELATED APPLICATIONS

This application is a continuation of U.S. application Ser. No. 16/282,167, now U.S. Pat. No. 10,933,243 B2, filed Feb. 1, 2019, which claims priority to Italian Patent Application Number 102018000002962, filed Feb. 22, 2018, both of which are hereby incorporated by reference in its entirety.

TECHNICAL FIELD

Described herein are apparatuses for treating neurological disorders by electric stimulation, in particular adaptive electric stimulation, and methods for processing neural signals acquired by an electric stimulation apparatus during the delivery of stimulation pulses. The methods described herein comprise suppressing stimulation artifacts in the acquired neural signals in order to extract neural activity data.

BACKGROUND

Deep brain stimulation, also known by the acronym DBS, is a therapeutic method that electrically modulates the activity of neuronal structures of the central nervous system. One or more DBS electrodes are implanted by neurosurgery into a patient's brain to deliver electrical stimulation to neurons in the brain area(s) surrounding the electrodes. Electric stimulation consists of generating a train of electrical pulses using a pulse generator and transmitting these pulses to the one or more implanted electrodes, which deliver these pulses to a brain area of interest. In some cases, electrical pulses have relatively high-frequency (>100 Hz), biphasic waveforms, having a cathodic phase followed by an anodic phase. The overall charge injected in the two phases is forced to be nil to avoid tissue damage. In conventional DBS systems, stimulation parameters such as amplitude, frequency and pulse width are constant over the time and can only be adjusted by a clinician during a scheduled clinic visit.

DBS is currently used for the treatment of multiple diseases, including Parkinson's disease. Such a method allows the functional autonomy of patients to be improved, thus offering a better quality of life. However, some patients still suffer from adverse motor symptoms and suboptimal control of clinical fluctuations. Such DBS related issues may be mitigated by adjusting stimulation parameters. For instance, the adjustment of stimulation parameters can avoid motor symptoms induced by DBS (Bronstein et al., 2011) stimulation-induced hemiballism (Limousin et al., 1996), motor side effects such as dyskinesia (Hamani et al., 2005), speech and gait impairment (Bronstein et al., 2011). Moreover, it has been observed in a long-term follow-up study that the greater the number of follow-up visits for DBS parameter adjustment, the more promising the DBS clinical outcomes (Moro et al., 2006).

The recent research and technological innovations in the field of neurophysiology, neuroimaging, and neural engineering provided new opportunities to explore the Parkinson's disease pathophysiology and DBS mechanisms. With these developments, the idea of a DBS system which can adapt stimulation parameters over time in relation to symptom fluctuations and adverse effects, achieved a high interest (Burgess et al., 2010, Rosin et al., 2011, Santaniello et al., 2011) and has been generally referred to as Adaptive DBS or Closed-loop DBS.

A closed-loop paradigm adapts stimulation parameters based on a control variable that may represent the patient's clinical state and its symptoms. U.S. Pat. No. 7,277,758 describes an apparatus for treating neurological disorders which is configured to adapt the stimulation parameters to the clinical state of the patient by recording a physiological marker, also known as biomarker, as a control variable. Other approaches have been proposed in the literature based on different control variables: neurochemical signals (Chang S Y et al., 2013), single and multi-unit activity based on micro-electrode arrays (Rosin et al., 2011), electrocorticography (Hemptinne et al., 2015), surface electroencephalography, surface electromyography and accelerometers.

Adaptive DBS techniques may use the low-frequency oscillatory components of the electrical activity of the neuronal population around the electrode, known as local field potentials (LFPs), as a control variable for adjusting stimulation parameters. LFPs have been found, in some circumstances, to correlate with the patient clinical state (Priori et al., 2004, Eusebio et al., 2011, Kuhn et al., 2009). Some DBS systems may be able to record LFPs using the electrodes that are also used for stimulation. The amplitude of LFPs may contain information representing the state of a specific brain region. For example, in Parkinson's disease, excessive synchronization of the basal ganglia network in the beta frequency band (12-35 Hz) has been linked to motor impairments (Kuhn et al., 2009). The power value of the beta band has been therefore proposed as control variable for adaptive DBS (Priori et al., 2013).

LFPs recorded from DBS electrodes are low-amplitude signals in the microvolt range (Yoshida et al., 2012) having frequencies of interest as low as 1 Hz. Especially in implantable devices, the development of recording systems that are able to both measure these low-amplitude, low-frequency signals while delivering electrical stimulation can be difficult because of the restricted power and space budget that generally impacts on the noise performance. To achieve appropriate space and power dimensioning, the recording circuits of the prior art have been developed as application-specific integrated circuits (ASIC) implemented using low voltage CMOS circuitry. More specifically, prior art recording circuits make use of operational amplifiers with MOS input transistors. This implies a limit in their downscaling due to the several non-ideal effects (e.g., 1/f noise, thermal noise, DC offset) inherent in size reduction of device technology operating at low voltages.

A solution for an analog front-end that may handle input noise while satisfying size and power consumption criteria for an implantable device has been proposed in U.S. Pat. No. 7,847,628, which describes a chopper amplifier for modulating the target signal to higher frequency where the 1/f flicker noise is negligible. The "chopper stabilization technique" used in U.S. Pat. No. 7,847,628 for removing the non-ideal effects of operational amplifiers consists in modulating the input signal to very high frequencies (i.e., with respect to the signal frequency content) upstream from the amplifier. In this way, the flicker noise generated by the amplifier is not superimposed to the input signal. Downstream of amplification, the input signal is modulated back to its original frequency band with a suitable amplitude to dominate over the 1/f noise. This noise can be further reduced by low pass filtering.

However, concurrently recording LFPs and delivering stimulation may introduce an additional technical problem with respect to 1/f noise filtering. Sensing LFPs with concurrent stimulation is a desirable feature in adaptive DBS. Concurrently stimulating the brain region while recording LFP data may be used to track LFP power modulation over time and confirm or measure the efficacy of the stimulation.

The problem of recording local field potentials during deep brain stimulation consists in sensing a neural signal having an amplitude lower than 1 μV with a concurrent electric stimulus artifact in the order of tens of millivolts. The electric stimulus artifact is a voltage difference produced by the stimulating signal between two imperfectly matched recording electrodes. In order to be able to detect such low amplitude/low frequency neural signals, high gain amplification is desired. However, due to the presence of the stimulus artifact, high gain amplification can lead to the saturation of the recording chain. Since the stimulus artifact is included in the input signal from the beginning, i.e. before any modulations can take place, the chopper stabilization technique described in U.S. Pat. No. 7,847,628 reveals to be inappropriate to reduce the stimulus artifact. Moreover, moving the stimulus signal to the high frequencies may additionally introduce the problem that the high frequency components of the stimulus artifact interact with the "chop" harmonics.

To mitigate the problem of the stimulus artifact, Stanslanski et al. 2011 describe a solution making use of a first stage implemented as the analog front-end described in U.S. Pat. No. 7,847,628 followed by a second stage comprising a conventional low-pass filter (U.S. Pat. No. 9,888,861, Stanslanski et al., 2011). However, after low pass filtering, the signal still suffers of residual stimulation interferences, namely residual interferences due to the stimulus artifact, as described in detail below.

A different solution approach to this problem provides for a system comprising a low-gain differential stage followed by a low-pass filter and a final amplification stage. Keeping the differential gain low may help to avoid saturation and may facilitate amplification of the neural signal above the input referred noise of the low-pass filter. After low-pass filtering, the stimulation frequency components are significantly reduced or eliminated. This allows for the introduction of a single-ended stage to increase the gain without saturation and to adjust the signal amplitude to the A/D converter dynamic range. A low-pass passive network before the differential stage may be introduced to further suppress the artifact before the first amplifier, if required by its gain/input dynamic range performance.

Although this solution has proven to be effective in recording LFPs during stimulation, some residual stimulation interference still persisted after low-pass filtering. Residual stimulation interference may occur in the form of an unwanted increase of the total power (signal included) as shown in FIG. 9a and/or spurious artifact tones in the band of interest for LFP recording (<40 Hz). Despite these residual stimulation interferences have been observed, their causes have not been determined yet. One attempt to manage the problem of reducing or eliminating such residual stimulation interference provided for normalization of the spectral content of the filtered neural signal by its total power. The main drawback of this method is that it can introduce a bias whenever physiological power spectral changes occur outside the observed frequency band. For instance, an increase of power in a frequency band different from the one chosen as control variable (i.e., beta band) may lead to an underestimation of the useful signal.

In alternative, Stanslanski and colleagues used a support vector machine (SVM) logic to introduce a linear separation between the same signals recorded with and without stimulation (U.S. Pat. No. 9,888,861, Stanslanski et al., 2011). The basic assumption of this method is that the effect of the stimulation on the band power is linear. However, even if the assumption is correct, SVM logic typically requires a large amount of patient-specific data to train the network and, moreover, it is not suitable for algorithms requiring a continuous changing of the stimulation parameters.

SUMMARY OF THE INVENTION

Applicant contemplated the problem of overcoming the above-mentioned drawbacks, and, in particular, of eliminating or substantially reducing the residual stimulation interferences affecting the neural signal after low-pass filtering in an apparatus for treating neurological disorders.

Within the scope of the above problem, the Applicant considered the objective of allowing reliable sensing with concurrent stimulation in an apparatus for treating neurological disorders providing adaptive electrical stimulation.

Therefore, the technical problem consists in devising apparatuses and methods for processing the neural signal capable of recording LFPs during stimulation by suppressing the stimulation artifact and reducing or eliminating residual stimulation interference (e.g., unwanted increase of the total power and/or spurious artifact tones in the low frequencies (<40 Hz)) that may affect the neural signal, thereby providing reliable and accurate acquisition of neural signal data for adapting the electrical stimulation with an architecture suitable for an implantable system and for industrial manufacturing process reliability (i.e. optimized in terms of space and power consumption).

One variation of an apparatus for treating neurological disorders may comprise at least one electrode implantable in the brain of a patient, and a processing and stimulation device connected to the at least one electrode. The processing and stimulation device at least comprises a stimulation module configured to generate a stimulation signal to be sent to the at least one electrode, and an acquisition module configured to acquire local field potentials (LFPs) characteristic of cerebral activity (e.g., neural signal) measured by the electrode from the brain of the patient. The acquisition module at least comprises a front-end block configured to amplify the potential difference of its input signals ($V_{1a}$, $V_{2a}$) and to filter a stimulus artifact by cutting off frequencies above a predefined frequency band, characterized in that the front-end block comprises a multi-stage fully-differential switched capacitor circuit (e.g., an integrated circuit) configured for discrete-time signal processing.

For the first time, based on mathematical simulation and in vitro testing, Applicant was able to determine the genesis of the above discussed residual stimulation interferences. Applicant realized that the real stimulus signal is not an ideal periodic monophasic/biphasic square wave with only high frequency components, but it carries additional noise even in the low frequencies (i.e. having frequency components that overlap with the frequency spectrum of LFPs). This additional noise in the low frequencies may be converted into a differential artifact by imbalances on the recording electrodes and by the finite common mode rejection of the acquisition system.

Moreover, Applicant observed that the finite common mode rejection of the acquisition system causes the conversion of the common mode noise, superimposed onto the stimulus signal, into a differential form, thus being amplified and acquired. Accordingly, Applicant identified the importance of optimizing the common mode rejection of the multi-stage front-end.

Described herein are variations of LFP acquisition modules (i.e., electrical circuitry) that allow reliable LFP signal sensing with concurrent stimulation in an apparatus for electrical deep brain stimulation. One variation of an acquisition module may comprise a high-order low pass filter (i.e., corner frequency<100 Hz) that reduces or eliminates residual stimulation interference, facilitates common mode rejection, and is operable under the size and power consumption constraints of an implantable device. An acquisition module may comprise a switched-capacitor based, fully-differential, multi-stage architecture that is configured to process a discrete signal.

Applicant has identified that the use of a fully-differential architecture based on switched capacitors technology may provide good common mode rejection and makes possible the implementation of a very low-frequency filter corner, while satisfying the size constraints of an implantable device.

The fully-differential circuit architectures comprising switched capacitor technology described herein may be configured to use discrete-time processing methods to help mitigate the 1/f noise and DC offset without impacting (e.g., increasing) the circuit size.

Also described herein is a method for processing neural signals collected by an apparatus for treating neurological disorders or DBS system. In one variation, the method may comprise amplifying and pre-filtering the neural signal using a first stage comprising a fully-differential switched capacitor circuit (e.g., an integrated circuit) configured for discrete-time signal processing, and filtering the amplified and pre-filtered signal by cutting off signals above a predetermined frequency band using a second stage comprising a fully-differential switched capacitor circuit (e.g., an integrated circuit) configured for discrete-time signal processing. Preferably, at least one of the step of amplifying and pre-filtering the neural signal and the step of filtering the amplified and pre-filtered signal comprises correlated double sampling (CDS). Optionally, the step of amplifying and pre-filtering the neural signal may comprise amplifying the neural signal to a value greater than an input-referred noise of the second stage.

Advantageously, the method for processing neural signals described herein achieves the technical effects described above with regard to the apparatus for treating neurological disorders.

While some variations may comprise at least one of the above aspects and/or may have at least one of the following preferred features, any of the features described herein may be combined with each other as desired to meet specific implementation purposes.

In one variation of an apparatus described herein, a multi-stage front-end block may comprise a pre-filter stage and a suppression filter stage positioned downstream from the pre-filter stage. The acquisition module may comprise an analog-to-digital (A/D) converter block that may be in downstream communication with the front-end block. In some variations, the front-end block may comprise a two-stage, fully-differential switched capacitor circuit configured for discrete-time signal processing in order to maximize the common mode rejection ratio of the acquisition system. Accordingly, the differential signal may be transmitted in its discrete-time form from the front-end block to the A/D converter, which converts the analog input signal into a digital output signal.

In some variations, the pre-filter stage of the front-end block may comprise a fully-differential low-pass switched capacitor filter, clocked at a first clock frequency. Accordingly, the step of amplifying and pre-filtering the neural signal may be performed using the first fully-differential switched capacitor filter, clocked at the first clock frequency. Advantageously, the pre-filter stage provides amplification while filtering out high-frequency components of the signal that can cause aliasing effects, i.e., the pre-filter stage may be configured to perform an antialiasing function.

In some variations, the suppression filter stage of the front-end block may comprise a fully-differential low-pass switched capacitor filter, clocked at a second clock frequency. The first clock frequency of the pre-filter stage may be greater than the second clock frequency of the suppression filter stage. In some variations, the first clock frequency may be about 1 KHz or more. The second clock frequency may be less than half of the first clock frequency.

Preferably, the pre-filter stage may comprise a filter having an order lower than an order of the filter of the suppression filter stage. In some variations, the filter of the suppression filter stage may have an order of at least three or more. The pre-filter stage may comprise a low pass filter having a first cut-off frequency in the range between the minimum stimulation frequency (e.g., about 50-250 Hz), and the second clock frequency. For example, the first cut off frequency may be greater than about 50 Hz.

In some variations, the suppression filter stage may comprise a filter having a second cut-off frequency in the range between the maximum frequency component of the neural signal (e.g., about 35-40 Hz) and the frequency of the stimulus artifact (e.g., about 50-250 Hz). Accordingly, the step of filtering the amplified and pre-filtered signal may be performed using the second fully-differential switched capacitor filter, clocked at the second clock frequency. The first cut-off frequency of the pre-filter stage is preferably greater than the second cut-off frequency of the suppression filter stage.

Preferably, the second cut-off frequency is in the range of about 35-250 Hz.

Distributing the functionalities among at least two stages (e.g. the anti-aliasing filtering to the pre-filter and the stimulation artifact rejection to the suppression filter), allows to achieve an optimal trade-off between performances and size/complexity of the circuit.

In some variations, a fully-differential switched capacitor pre-filter stage and/or a suppression filter stage may be implemented as ladder filters employing switched capacitor integrators in an active emulation of a lossless LC ladder structure.

In detail, the fully-differential switched capacitor filter stages (pre-filter and/or suppression filter) may be implemented using CMOS technology. Advantageously, these filter architectures may achieve a very precise response, featuring very low sensitivity to spreads in component values, and a wide dynamic range while requiring small chip area, low-power consumption, and relatively low-performance operational amplifiers.

In a preferred embodiment, the fully-differential switched capacitor pre-filter and/or suppression filter comprises basic building units having fully-differential bilinear switched capacitor integrators. Advantageously, the pre-filter and/or suppression filters that comprise fully-differential bilinear switched capacitor integrators may help increase the common-mode rejection ratio (CMRR) at the frequencies of interest (i.e. at the frequencies of a recorded neural signal and/or any neural activity signal, for example, in the range of about 1 Hz to about 40 Hz, e.g., from about 1 Hz to about 35 Hz).

In some variations, basic building units may comprise two inputs which are alternatively connectable to one end of two input capacitors, the other end of the two input capacitors being configured to alternatively connect to a reference voltage source or, each respectively, to one of two inputs of an amplifier, each input of the operational amplifier being connectable to one respective output of the operational amplifier through interposition of a first and a second feedback capacitor, respectively. This circuit arrangement may help to further increase the CMRR and facilitate the reduction and/or elimination of noise (e.g., from the stimulation artifact and/or 1/f noise) to extract neural signals of interest (e.g., neural activity data).

In some variations, the basic building units may be configured to implement a correlated double sampling (CDS) technique.

In some variations, the basic building units may optionally comprise a third and a fourth feedback capacitor connected in parallel to the first and second feedback capacitors, respectively.

In some variations, the first and/or the second clock signal may be configured to time the alternative connection and disconnection of the third and fourth feedback capacitors to the input signal of the amplifier.

The timing of the connections between the input signal and the input capacitors, the input capacitors and the inputs of the amplifier, the feedback capacitors and the amplifier, may be controlled by the first and/or second clock signal with a specific phase for each connection stage for implementing the correlated double sampling (CDS) technique.

The connection between the input signal and the input capacitors and the connection between the feedback capacitors, may be controlled by first clock signals that are respectively in opposition of 180°. The connection between the input capacitors and the input of the amplifier are controlled by second clock signals that are delayed compared to the first clock signals and respectively in opposition of 180°.

Advantageously, the correlated double sampling (CDS) technique reduces noise density at low frequency and is thus particularly suitable for very low frequency applications of switched capacitor filters, wherein the dominant noise is the 1/f noise component of the operational amplifier. The CDS technique allows to implement a very compact pre-filter stage still effectively removing the nonideal 1/f noise. In fact, switched capacitors circuits allow to implement the CDS technique by adding switches.

In some variations, the output of the suppression filter stage may be fed differentially to the A/D converter. Accordingly, in some variations, the acquisition module further comprises an A/D converter block connected downstream from the front-end block. The A/D converter block may preferably comprise a delta-sigma converter.

In some variations, the A/D converter block may comprise a fully-differential switched-capacitor circuit (e.g., an integrated circuit).

In some variations, the A/D converter comprises a first sampling stage, followed by a filter stage configured for removing the quantization noise, and a decimation stage.

In some variations, the stimulation device may further comprise a control module configured for implementing an adaptive control of the stimulation module based on the signal acquired by the acquisition module.

In some variations, the acquisition module may optionally comprise a functional module upstream from the front-end configured to receive an input synchronization signal from the stimulation module for disconnecting or grounding the inputs of the front-end block during stimulus pulses generated by the stimulation module.

To facilitate sensing during stimulation, this functional module disconnects or grounds the inputs of the subsequent processing module during each stimulation pulse coming from the acquisition chain. Disconnecting or grounding the inputs during each stimulus and re-connecting them to the recording system after each stimulation pulse provides for an additional suppression/mitigation of the stimulus artifact, thus unburdening the attenuation requirements at the level of the second suppression filter stage.

In some variations, the acquisition module may further comprise a second functional module configured to suppress high frequencies in a signal produced by the operation of the first functional module.

In some variations, the acquisition module may also comprise a third functional module configured to provide high-pass filtering so as to mitigate offset potentials at least at one electrode (e.g. common mode and DC differential potentials), e.g., produced by the differences in the interface electro-chemical balances.

In some variations, the stimulation device may comprise a control module configured to implement an adaptive control of the stimulation module based on the signal acquired by the acquisition module. The control module may advantageously utilize the acquired neural signal to determine the feedback of parameters of the stimulation signal in order to adapt the therapy to patient neural activity data, which may represent a patient symptomatic state.

In some variations, the stimulation device may comprise at least one electro-catheter implantable in the brain of a patient and the at least one electrode may be located on the at least one electro-catheter. The at least one electro-catheter may comprise at least three electrodes, wherein at least two electrodes act as sensors that are configured to acquire neural signals in a patient brain region and to send the acquired neural signals to the acquisition module, and at least one electrode receives a stimulating signal from the stimulation module to deliver electrical stimulation to the patient brain region.

BRIEF DESCRIPTION OF THE DRAWINGS

With reference to the attached drawings, further features and advantages of the present invention will be shown using the following detailed description of some of its preferred embodiments.

According to the above description, the several features of each embodiment can be unrestrictedly and independently combined with each other in order to achieve the advantages specifically deriving from a certain combination of the same.

FIG. 6 is a schematic view of a second preferred embodiment of an integrator forming a basic building unit used for implementing the filter stages of the front-end block of the acquisition module of FIG. 2a and FIG. 2b, and FIG. 6a depicts a timing diagram of clock signals that control the operation of the integrator of FIG. 6;

FIGS. 8a-d are graphs illustrating the frequency components of a signal at various stages within the front-end block of the acquisition module of FIG. 2a and FIG. 2b;

DETAILED DESCRIPTION

Figure 1:
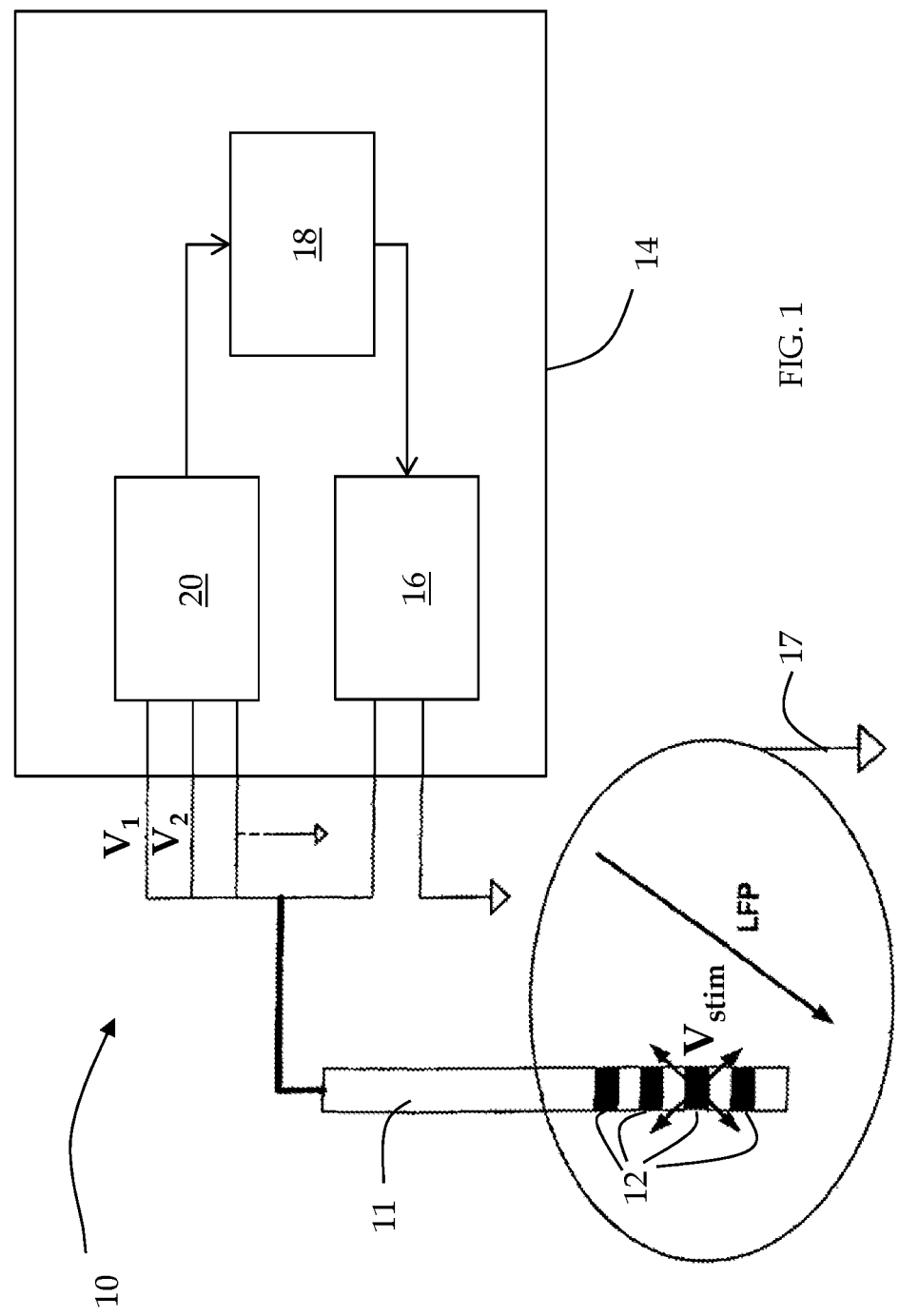
FIG. 1 shows a schematic view of a preferred embodiment of a brain stimulation apparatus for treating the neurological disorders.

In the figures and in the following description, identical reference numerals or symbols are used to indicate constructive elements with the same function. Moreover, for the sake of clarity of illustration, it is possible that some reference numerals are not repeated in all of the figures. While examples and variations of the invention are depicted and described herein, it should be understood that there is no intention to limit the invention to the specific examples and variations embodiments described below, but on the contrary, the invention is meant to cover all the modifications or alternative and equivalent implementations which fall within the scope of protection of the invention as defined in the claims.

Expressions like "example given", "etc.", "or" indicate non-exclusive alternatives without limitation, unless expressly differently indicated. Expressions like "comprising" and "including" have the meaning of "comprising or including, but not limited to" unless expressly differently indicated. Further, a "module" or a "functional module" as referenced throughout may refer to an assembly of electrical circuitry and/or electrical components that are arranged and connected to perform one or more functions as described herein, and/or may refer to a special purpose computer that is programmed to perform the functions described herein.

With reference to FIG. 1, one variation of an apparatus for treating neurological disorders is shown, wholly indicated with 10.

In particular, the apparatus illustrated in FIG. 1 is suitable for the adaptive deep brain stimulation being configured to detect biopotentials (e.g., local field potentials or LFPs) from a stimulating electrode or from contiguous electrodes, for correlating such signals to the stimulation effects and/or for adapting stimulation parameters in order to facilitate patient therapy.

The apparatus for treating neurological disorders 10 comprises at least one probe or electro-catheter 11 configured to be implanted in the brain of a patient to administer electrical stimulation. The probe or electro-catheter 11 may comprise at least three metallic contacts or leads accessible through external connections, also called electrodes 12. However, in other variations, the electrodes may not be located on the same electro-catheter (e.g., an apparatus for adaptive DBS may comprise two or more electro-catheters and the electrodes may be located on two different electro-catheters).

The apparatus for treating neurological disorders 10 may comprise one or more implantable probes where each probe may comprise one or more electrodes. The apparatus 10 may also comprise a connector or probe extension for each of the implantable probes. A probe (e.g., probe 11) may have a distal portion and a proximal portion. The one or more electrodes (for delivering electrical stimulation and/or neural activity data acquisition) are located on the distal portion and one or more connector contacts are located on the proximal portion, and one or more wires within the probe electrically connect the electrodes with the connector contacts. A probe 11 may comprise any number of electrodes 12, for example, 1, 2, 3, 4, 5, 6, 8, 10, 12, 16, 24, 36, 48, 64, 96, etc. and a corresponding number of connector contacts. A probe extension may have a distal portion having a connector block with a receptacle housing enclosing one or more conductive contacts, a proximal portion having stimulation device (e.g., apparatus 10) connector contacts, where each of the stimulation device connector contacts corresponds with a conductive contact in the receptacle housing via one or more wires, and an elongated body between the proximal portion and the distal portion. A probe extension may comprise any number of conductive contacts, for example, 1, 2, 3, 4, 5, 6, 8, 10, 12, 16, 24, 36, 48, 64, 96, etc. and a corresponding number of stimulation device connector contacts. The number of conductive contacts of the probe extension may be the same as, or greater than, the number of electrodes on the probe to which the probe extension is connected. The distal portion of the probe may be implantable into the target brain region, while the proximal portion of the probe may extend outside of the brain tissue and connect with a distal portion of a probe extension. The receptacle housing of the probe extension may be configured to retain the proximal portion of the probe such that the connector contacts of the probe electrically connect with the conductive contacts of the probe extension such that the electrodes at the distal portion of the probe are electrically coupled to the stimulation device connector contacts at the proximal portion of the probe extension. The stimulation device connector contacts may be configured to be coupled to a port or connector of a processing and stimulation device 14 (e.g., a header interface). In some variations, the receptacle housing may comprise an attachment mechanism to engage or retain the proximal portion of the probe within the receptacle housing. Optionally, the probe extension may comprise a connector sleeve or boot comprising an electrically insulating material that is disposed over at least a portion of the receptacle housing to help electrically isolate the connector contacts of the probe and the conductive contacts of the probe extension from surrounding tissue. The elongated body of the probe extension may have a constant diameter between the distal portion and the proximal portion, or may have a varying diameter along its length. For example, the diameter of a segment of the elongated body may be larger (e.g., thicker) where that segment is intended to be located at the interface between brain tissue and the skull or skin. This may help reduce excessive twisting, torqueing, and/or bending of the wires within the elongated body of the probe extension, thereby reducing the mechanical wear on the wires and/or helping to prolong the usable life of the probe extension.

While the apparatus for treating neurological disorders 10 depicted in FIG. 1 comprises a probe 11 having four metallic contacts or electrodes 12, other variations of probes may comprise any number of electrodes (e.g., 1, 2, 3, 4, 5, 6, 7, 8, 9, 10, 12, 16, 18, 20, 25, 30, 36, 48, or more). As described previously, an apparatus for treating neurological disorders 10 may comprise any number of probes (e.g., two or more), where each probe may have any number of electrodes. For example, an apparatus for treating neurological disorders 10 may comprise a first probe with a first electrode and a second probe with a second electrode. In use, the first probe may be implanted in a first brain region and the second probe may be implanted in a second brain region (e.g., for bilateral stimulation). In another variation, an apparatus for treating neurological disorders 10 may comprise two probes, where each probe may have four electrodes (for a total of eight channels) or may have eight electrodes (for a total of sixteen channels).

In one variation, a probe 11 may comprise multiple electrodes where a first electrode is a stimulating electrode that delivers electrical stimulation and a second electrode is a measurement electrode that acquires neural activity signals. For example, a first plurality of electrodes (which may or may not be adjacent to each other) may be used for stimulating and a second plurality of electrodes (which may or may not be adjacent to each other, or may be arranged in alternating fashion with the first plurality of electrodes) may be used for acquiring neural activity signals. Alternatively or additionally, the same electrode(s) may be used for both neural activity signal acquisition and electrical stimulation simultaneously or sequentially. DBS probes may comprise one or more cylindrical or disc-shaped electrodes having a height from about 0.5 mm to about 3 mm, e.g., about 1.5 mm, and a diameter from about 0.5 mm to about 2 mm, e.g., about 1.27 mm. In some variations, DBS probes may comprise two or more cylindrical electrodes (for example, 2, 4, 6, 10, 12, 15, 16, 20, etc. or more electrodes). Alternatively or additionally, DBS probes may comprise planar electrodes and/or sharp electrodes having a geometry selected at least in part based on the target neural structure or brain region. The spacing between two electrodes may be from about 0.25 mm to about 2 mm, e.g., about 0.5 mm, and optionally, an insulator may be disposed between two electrodes and/or around an electrode to reduce electrical coupling or cross-talk between electrodes. An insulator may comprise, for example, polyurethane and/or polyimide and/or the like. The electrodes may be made of any metal or any metallic alloy, for example, a platinum-iridium alloy.

In the embodiment illustrated in FIG. 1, the electrodes 12 are connected to a processing and stimulation device 14 that comprises three functional modules connected together in a feedback and interoperating configuration: a stimulation module 16, a data acquisition module 20 and a control module 18.

In one variation, the stimulation device 14 may comprise sixteen channels, which may be connected to two probes each having eight electrodes, or four probes each having four electrodes, or eight probes each having two electrodes, etc. There may be fewer electrodes than channels, for example, although the stimulation device 14 may be configured to accommodate sixteen channels (e.g., for sixteen stimulation and/or LFP acquisition electrodes), a particular instance of an apparatus for treating neurological disorders 10 or DBS system may comprise eight electrodes (e.g., two probes each having four electrodes) or four electrodes (e.g., a single probe having four electrodes).

The stimulation module 16 is adopted to generate a stimulation signal and to send it to the electrodes 12. The stimulation module 16 may comprise pulse or function generator comprising a voltage source and/or current source and circuitry configured to produce electrical pulses with certain parameter values determined by a user and/or controller, and may also comprise wires that transmit the electrical pulses to the probe, which deliver the electrical pulses to the brain region.

In some variations, the stimulation module may comprise a waveform generator (e.g., a pulse or function generator), a current controller, and a multiplexer, one or more of which may be configured to receive command signals from the control module or main processor 18. The command signals may comprise electrical stimulation parameter data, including, but not limited to, stimulation amplitude, pulse width, pulse frequency, duty cycle, and/or the specific probe(s) and/or electrode(s) from which electrical stimulation with the specified parameters is to be delivered. The current controller may be configured to set an electrical stimulation amplitude specified by the command signals, and/or the waveform generator may be configured to generate current or voltage pulses having the pulse width and/or pulse frequency specified by the command signals. The multiplexer may be configured to electrically connect the probes and/or electrodes specified by the command signals with the current controller and/or waveform generator. In some variations, the multiplexer may comprise a multiplexer array that may be configured according to command signals from the main processor so that the electrical pulses from the waveform generator may be channelled to the selected probes and/or electrodes. The connectivity between the waveform generator and the electrodes may be arranged by the multiplexer in a monopolar stimulation configuration and/or a bipolar stimulation configuration. In a monopolar configuration, one or more electrodes may be connected to one or more active (e.g., positive) terminals of the waveform generator (with a return pad placed elsewhere on a patient). In a bipolar configuration, a first set of one or more electrodes may be connected to one or more active (e.g., positive) terminals of the waveform generator while a second set of one or more electrodes (e.g. distinct from the first set of electrodes) may be connected to one or more return (e.g., negative) terminals of the waveform generator.

In some variations, the stimulation module 16 may be configured to generate a stimulation signal $V_{stim}$ that may be characterised by a set of parameters, and to transmit the stimulation signal $V_{stim}$ to one or more of the electrodes 12. For example, the stimulation module 16 may comprise a pulse generator having a current source (and/or voltage source) that generates electrical signals that have parameters specified by a user and/or the control module. In some variations, a pulse generator may form output pulses having specified amplitude, frequency and/or pulse width or duration values. Optionally, a pulse generator may generate a pulse sequence having two pulses or more pulses repeated with a duty cycle specified by a user and/or the control module 18, and the control module 18 may adjust the pulse duty cycle in accordance with one or more properties of the acquired neural activity signals (e.g., any of the patterns or properties described herein).

The data acquisition module 20 is responsible for the acquisition of a signal representative of the cerebral activity coming from the brain of the patient, e.g. LFP signals that may represent the cerebral activity in the brain region where the probe 11 is implanted. The acquisition module 20 is in electrical communication with the probe 11 which may be, in some variations, the same probe used to electrically stimulate the brain region. The acquisition module 20 and/or the probe 11 may be configured to acquire neural activity signals, such as local-field potentials (LFPs), resulting from the activity of the brain region in proximity to the probes 11. The acquisition module 20 may comprise an acquisition processor and memory that stores and analyzes the acquired neural activity signals.

The control module 18 implements an adaptive control of the stimulation module 16 based on the signal acquired by the acquisition module 20. The control module may have circuitry configured to facilitate communication between the acquisition module 20 and the stimulation module 16, coordinate signalling between the acquisition module 20 and the stimulation module 16, and/or to perform additional computations on the acquired neural activity signals.

The control module 18 may be part of either the acquisition module or the stimulation module, or may be a separate module. In some variations, the control module comprises circuitry configured to regulate/coordinate the operation of the stimulation module based on signals from the acquisition module (e.g., based on LFP signals indicative of neural activity). The control module may have a control module (main) processor and memory that analyzes and stores the acquired neural activity signals and/or signals from the acquisition module. In some variations, the control module may comprise circuitry that regulates the power supplied to the stimulation module, for example, in coordination with the electrical stimulation parameters determined by the acquisition module and/or the acquired neural activity signals. The properties or parameters of the electrical stimulation may be determined by the acquisition module and/or the control module. For example, the processors of the acquisition module and/or the control module may analyze the acquired and/or stored neural activity signals to identify variations or changes in the patterns or characteristics of neural activity signals. The control module may provide command signals to the pulse generator of the stimulation module to change the parameters of the electrical stimulation according to the changes in the neural activity signals detected or extracted by the acquisition module. The control module may also comprise a battery (e.g., a rechargeable battery), and circuitry configured to charge and/or measure the charge remaining on the battery. For example, the control module may comprise a rechargeable battery, an inductive link for charging the battery and an inductive coil for facilitating the energy transfer between an external charging device and the stimulation device (which may be implanted in the patient). Optionally, the control module may comprise wireless transmission interface (e.g., a transceiver) including an RF chip and an RF antenna for signal transmission between the implantable stimulation device and an external device. In some variations, the acquisition module may comprise a processor that is configured to calculate the spectral power values of acquired neural activity signals, and the calculated power values may be transmitted to the control module, and the control module processor may be configured to derive stimulation parameters according to the power values and general command signals to the pulse generator to adapt or adjust the parameters of the electrical stimulation. Optionally, the control module may comprise additional sub-modules with circuitry configured for power supply management, electrode impedance checking, and/or calibration and/or diagnostic analyses (e.g., troubleshooting) of the stimulation module.

Going back to the acquisition module 20 of FIG. 1, its main function is to measure the electric field variations of the local biopotentials directly sensing the difference between the electric potentials $V_1$ and $V_2$ referred to a common electrode 17 and to amplify such difference so as to reach a voltage level useful for the analog-to-digital conversion necessary for the signal processing.

Accordingly, the acquisition module 20 may comprise input ports $V_1$ and $V_2$ that are each connected to different electrodes 12 on the probe 11 and electrical circuits that are configured to measure the electric field variations of the local biopotentials or local field potentials (LFPs) based on the signals from the input ports $V_1$ and $V_2$. Electrical circuits of the acquisition module may comprise one or more processing units or processors (e.g., a CPU, and/or one or more field-programmable gate arrays, and/or one or more application-specific integrated circuits) that may be configured to perform computational operations, one or more memory elements, one or more amplifiers, one or more filters, and/or one or more analog-to-digital converters.

Figure 2C:
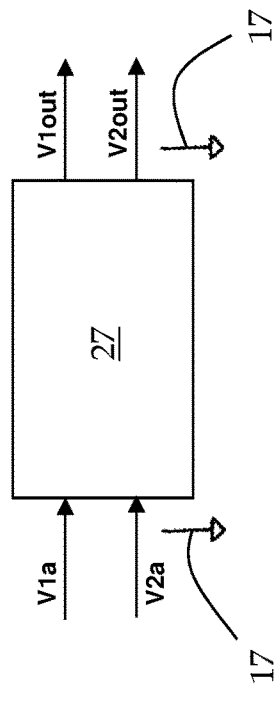
FIGS. 2c and 2d respectively shows a block diagram of the front-end block and of the A/D converter block of the acquisition module adopted by the apparatus of FIG. 1.
Figure 2A:
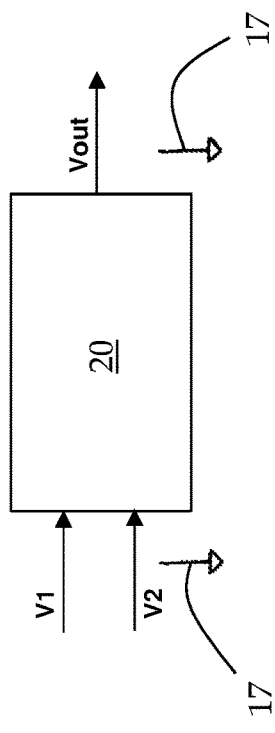
FIGS. 2a and 2b show two block diagrams of an acquisition module adopted by the apparatus of FIG. 1.
Figure 2B:
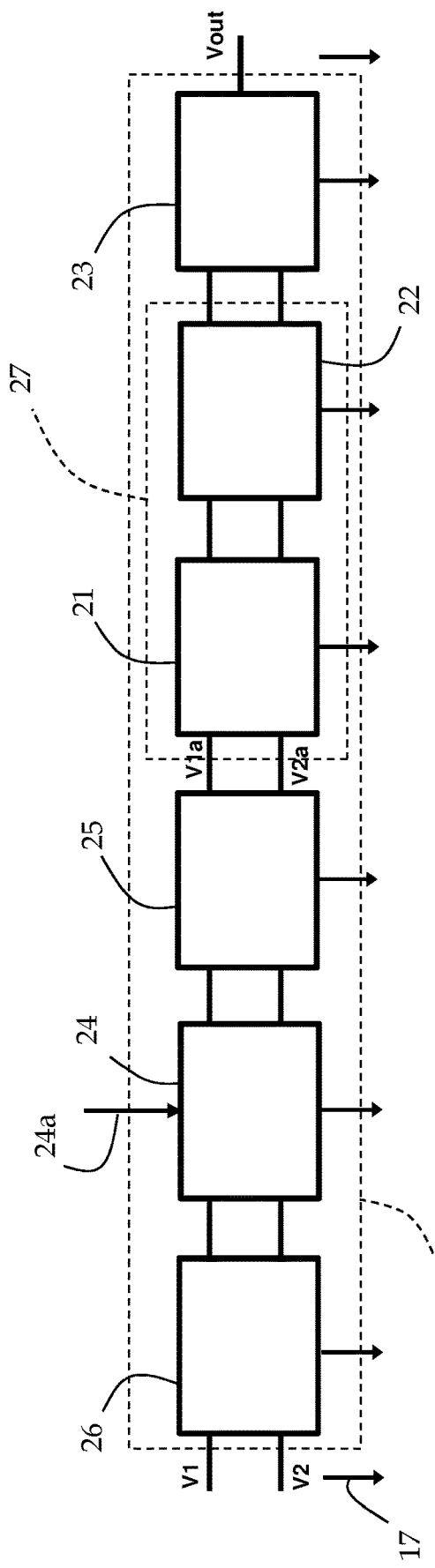

As depicted in FIG. 2b, the acquisition module 20 may measure electric field variations by sensing changes in the electric potentials $V_1$ and $V_2$ (e.g., difference(s) between $V_1$ and $V_2$, or values of $V_1$ or $V_2$ as referenced to a common or ground electrode 17) using a pre-amplifier and may amplify the changes (and/or any electric field variations) using an amplifier. The amplified output may be converted to a digital signal using an analog-to-digital converter, and the digital signal may be transmitted to the control module 18 (shown in FIG. 1) for further analysis and processing.

In some variations, the acquisition module 20 may comprise an acquisition processor that is configured to transform the acquired neural activity signals (e.g., LFPs) into spectral signals (e.g., spectral power values) that represent cerebral activity in the frequency domain (i.e., frequency-domain representation). For example, an acquisition processor of the acquisition module may be configured to carry out a Fourier Transform (e.g., a Fast-Fourier Transform or a Discrete-Fourier Transform) of the neural activity signals from input ports $V_1$ and $V_2$. The acquisition processor may comprise a general-purpose microprocessor that executes instructions from a software program to perform the frequency-domain signal transformation. Alternatively or additionally, the acquisition processor may comprise a digital signal processor (DSP) that has specialized electrical circuitry for performing the frequency-domain signal transformation. Alternatively or additionally, the acquisition processor may comprise an FPGA and/or ASIC configured for performing the frequency-domain signal transformation. Additionally, the acquisition processor(s) of the acquisition module 20 may be configured to calculate the power values of the neural activity signals in certain frequency bands of interest (e.g., the low-frequency band, alpha frequency band, beta frequency band, gamma frequency band, and/or any range of frequencies as may be desirable). In some variations, the acquisition processor may perform the power calculation in the time domain. The acquisition processor may comprise a band pass filter followed by a rectifier to perform the power calculation in the time domain. In some variations, the processor(s) of the acquisition module 20 may comprise an integral block and a derivative block (not illustrated) of the power values in order to highlight respectively slow and fast time changes of the power values. An integral or integration block may be configured to combine power values over time (e.g., by calculating an average value, which may be a moving average value) to help enhance slower changes or longer-term trends in power values. A derivative block may be configured to combine power values to help enhance faster or instantaneous changes in power values.

As shown in FIG. 2b more in detail, the acquisition module 20 comprises a front-end block 27 (shown in FIG.

2c) and an A/D converter block 23. In the depicted preferred embodiment, the A/D converter block 23 may comprise a delta-sigma converter.

The front-end block 27 may comprise a pre-filter stage 21 and a suppression filter stage 22. The pre-filter stage 21, the suppression filter stage 22 and the A/D converter block 23 may comprise one or more fully-differential switched-capacitor circuits. In detail, the pre-filter stage 21 may comprise a fully-differential switched-capacitor architecture which may be configured for both amplification and antialiasing filtering.

The suppression filter stage 22 may comprise a fully-differential switched-capacitor architecture which provides for low-pass filtering and additional amplification.

The A/D converter block 23 may comprise a switched-capacitor network which provides for amplification and analog-to-digital signal conversion.

Figure 3:
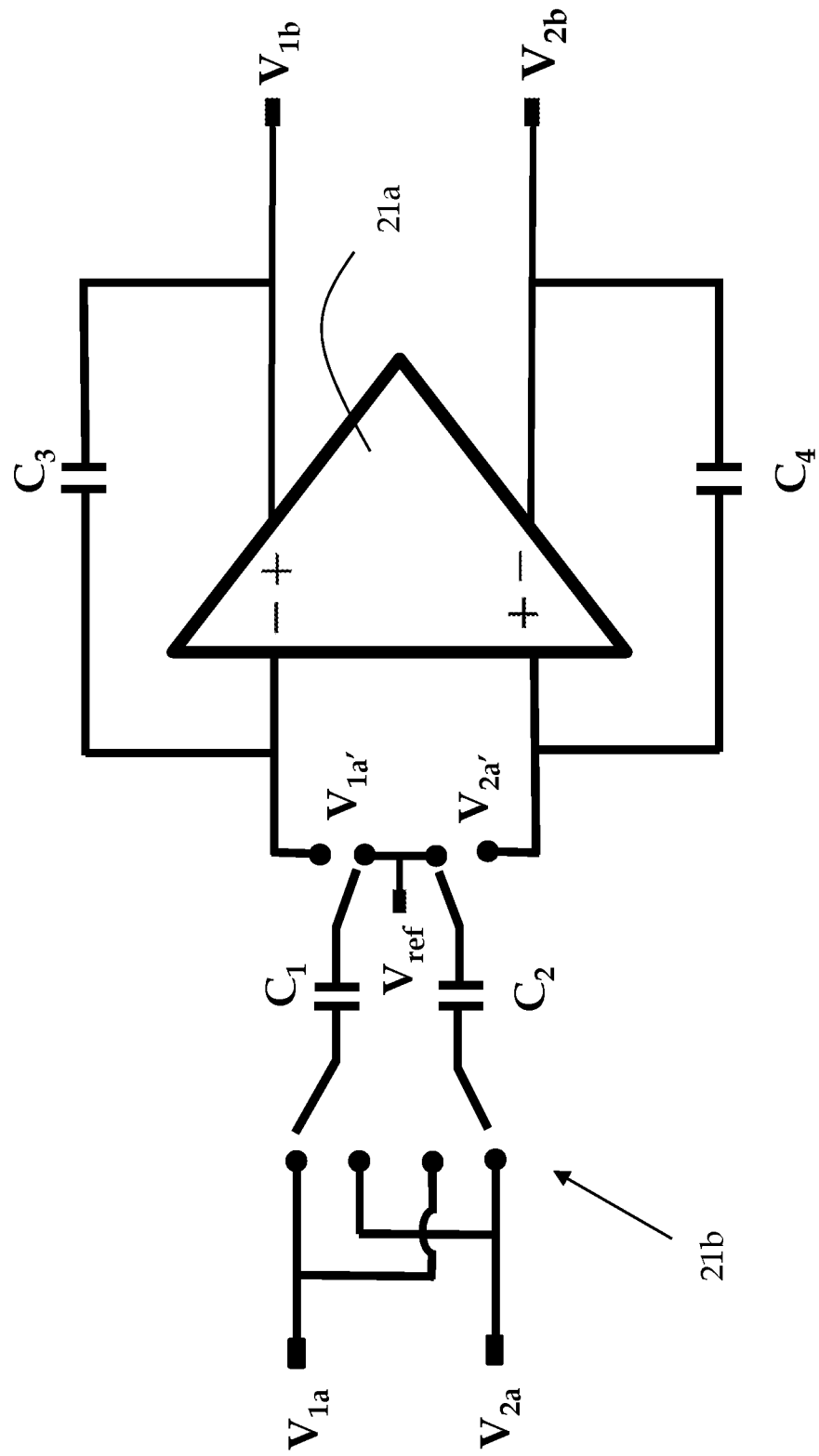
FIG. 3 is a schematic view of a first preferred embodiment of an integrator forming a basic building unit used for implementing the filter stages of the front-end block of the acquisition module of FIG. 2a and FIG. 2b.

The pre-filter stage 21 may be configured to differentially amplify the signal to a value greater than the input referred noise of the suppression filter stage 22 without compromising the minimum detectable signal (in the order of μV) and by avoiding the saturation of the recording chain. Accordingly, as schematically depicted in FIG. 3, the pre-filter stage 21 may comprise a fully-differential operational amplifier 21a, a plurality of input capacitors $C_1, C_2$ connected at its input terminals and feedback capacitors $C_3, C_4$ connected between its input and output terminals. The gain of the pre-filter stage 21 is configured by choosing the values of the input and the feedback capacitors. Variations of pre-filter stage circuitry are further described below.

Figure 4:
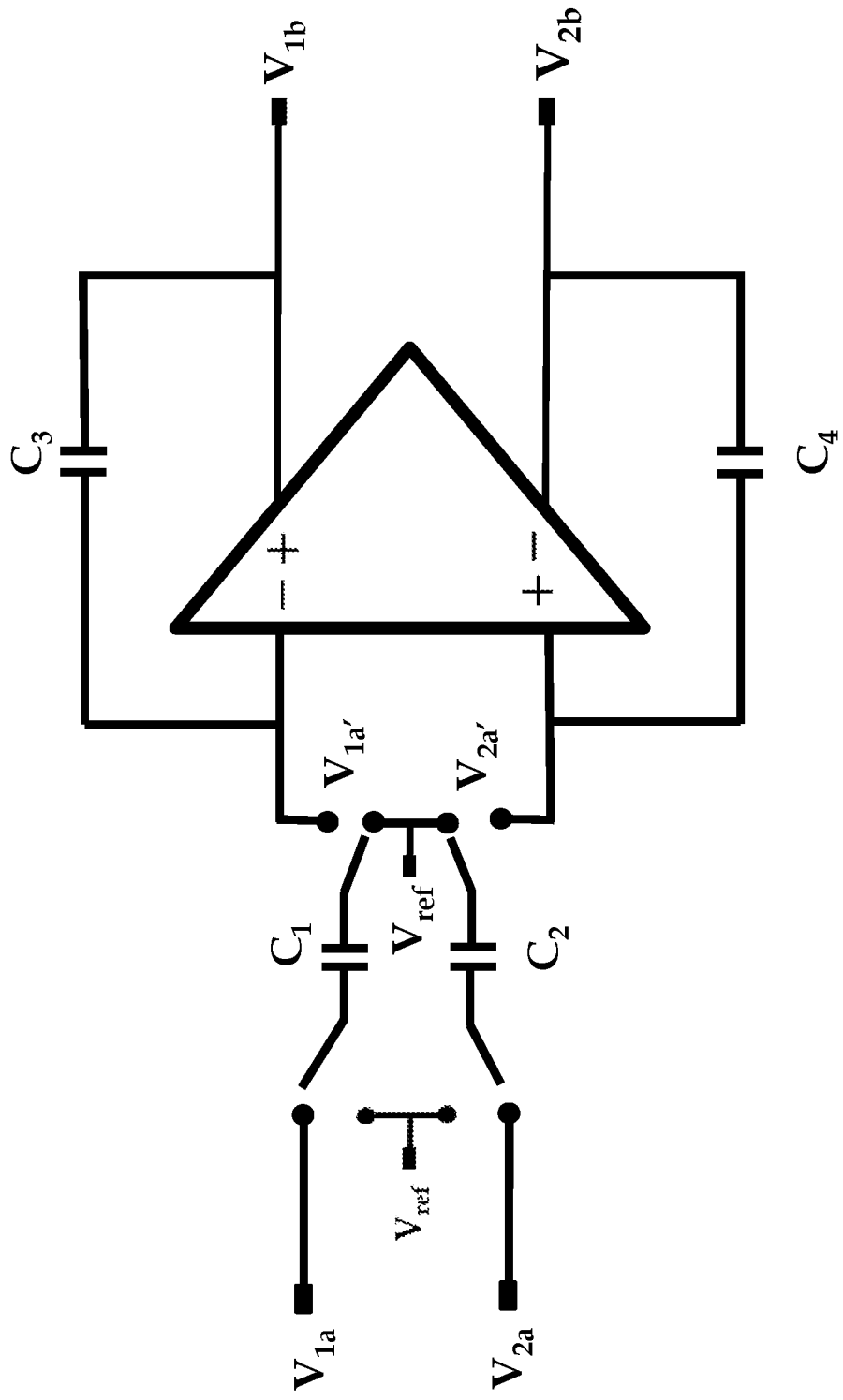
FIG. 4 is a schematic view of a conventional fully-differential switched capacitor integrator.
Figure 5:
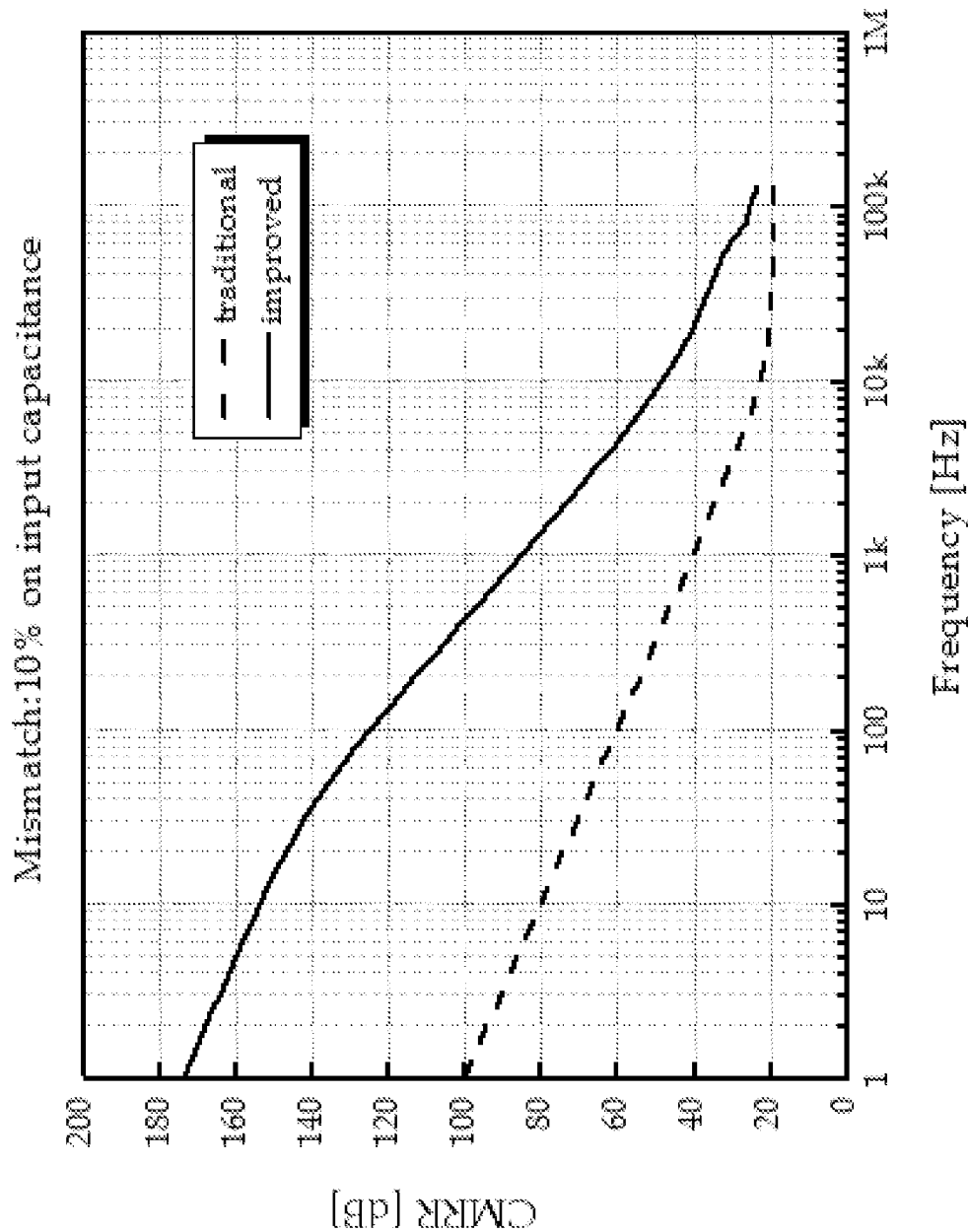
FIG. 5 is a plot that depicts the CMRR between the conventional switched capacitor integrator according to FIG. 4 and the improved bilinear fully-differential switched capacitor integrator according to FIG. 3 in the presence of a capacitive mismatch of 10% between input capacitances.

The pre-filter stage 21 and/or suppression filter stage 22 may comprise a ladder configuration of the fully-differential low-pass switched capacitor filters. The ladder configuration makes use of basic building units, such as those depicted in FIG. 3. In this variation, the basic building unit is a first-order bilinear switched capacitor integrator which allows an improvement of the CMRR at the frequencies of interest as compared to the CMRR of conventional integrators (FIG. 4). As shown in FIG. 5, the basic building unit of FIG. 3 achieves higher CMMR compared to the conventional integrator of FIG. 4.

The input network 21b of the used integrator (FIG. 3) adopts a parasitic insensitive switched capacitor configuration being each node of the switched capacitor connected between two voltage sources $V_{1a}$, $V_{2a}$, or between a common reference voltage $V_{ref}$ and virtual ground.

In this way a differential sampling can be performed by subtracting the negative from the positive signal at the front-end of the acquisition chain during each sampling period.

In detail, the inputs $V_{1a}$ and $V_{2a}$ are alternatively connected to one end of two input capacitors $C_1$ and $C_2$. The other end of the two input capacitors $C_1, C_2$ is alternatively connected to a reference voltage $V_{ref}$ or, each respectively, to one of two inputs of the fully-differential operational amplifier 21a. Each input of the operational amplifier 21a is connected to one respective differential output through interposition of a first $C_3$ and a second $C_4$ feedback capacitor, respectively; in this configuration, by setting the common mode of the inputs $V_{1a}$ and $V_{2a}$ equal to $V_{ref}$, the inputs $V^+$ and $V^-$ of the amplifier 21a are also polarized at this value for the whole sampling period.

A common mode feedback internal to the operational amplifier ensures that in any instant $V_{1b} = -V_{2b}$.

Assuming that the input voltages do not change for an overall sampling period T, the operating conditions of the circuit of FIG. 3 can be summarized by the following set of equations:

$$V_{1b} = (-V_{1a}z^{-1}C_1 + V_{2a}C_1) \times \frac{1}{C_3}$$

$$V_{2b} = (-V_{2a}z^{-1}C_2 + V_{1a}C_2) \times \frac{1}{C_4}$$

where z is the discrete-time variable used in signal-processing mathematics.

The circuit schematic shown in FIG. 3 has been generalized by making all the capacitors different. This extension is made to observe that mismatches do not affect the CMRR capabilities of the circuit. In real terms, a proper design would make $C_1 = C_2$ and $C_3 = C_4$.

The output signal $V_O$ is given by:

$$V_O = V_{1b} - V_{2b}$$

assuming that the input signal changes at a much lower frequency than the sampling rate, thus with $z^{-1} \cong 1$.

Accordingly:

$$V_O = -\left(\frac{C_1}{C_3} + \frac{C_2}{C_4}\right)(V_{1a} - V_{2a})$$

The advantage of this circuit can be simply seen from the last equation. If a common mode voltage $\Delta V_C$ is added to both the input voltages as follows $$V_{1a}' = V_{1a} + \Delta V_C$$

and $$V_{2a}' = V_{2a} + \Delta V_C,$$

ideally the common mode signal $\Delta V_C$ is cancelled in the output voltage $V_O$.

This property comes from the discrete-time approach of switched capacitor circuits.

In a real situation, in presence of an input capacitive mismatch $\Delta C_{12}$, the common mode input voltage $\Delta V_C$ is not totally rejected, but the bilinear switched capacitor integrator achieves a smaller differential output voltage (caused by $\Delta V_C$) compared to the traditional switched integrator of FIG. 4 with the same differential transfer gain. There is therefore an improvement in the common mode rejection, as shown in FIG. 5 with a 10% of mismatch on input capacitance.

However, this CMRR figure does not remain constant but decreases as the frequency increases because the condition $z^{-1} \cong 1$ does not hold anymore.

In the second preferred embodiment depicted in FIG. 6, the basic building unit is a first-order bilinear switched capacitor integrator configured to implement correlated double sampling (CDS). This allows to achieve, in addition to optimal CMRR at the frequencies of interest, also optimal rejection of DC offset and rejection of 1/f noise compared to the conventional integrator shown in FIG. 4.

Differently from the basic building unit of FIG. 3, in the basic building unit of FIG. 6 each input of the operational amplifier 21a is connected to one respective differential output through interposition of a first pair of feedback capacitors $C_3$ and $C_5$ and a second pair of feedback capacitors $C_4$ and $C_6$, respectively. More in detail, a third $C_5$ and a fourth $C_6$ feedback capacitor are connected in parallel to the first $C_3$ and second $C_4$ feedback capacitor, respectively. The feedback capacitor pairs $C_3,C_5$ and $C_4,C_6$ are alternatively connected or disconnected to the respective input of the amplifier 21a.

The timing of the connections between the inputs $V_{1a}$, $V_{2a}$, and the input capacitors $C_1,C_2$, the input capacitors $C_1,C_2$, and the inputs of the amplifier $V_{1a'}$, $V_{2a'}$, the pairs of feedback capacitors $C_3,C_5$ and $C_4,C_6$ and the inputs of the amplifier $V_{1a'}$, $V_{2a'}$, is controlled by a plurality of clock signals as shown in FIG. 6a (i.e., four clock signals Clk1, Clk2, Clk3, Clk4). The switch connectivity state (i.e., circuit nodes that are connected by the switch) during the high state of a particular clock signal is indicated by $\varphi_1$, $\varphi_2$, $\varphi_{1a}$, $\varphi_{2a}$.

Each clock signal of the plurality of clock signals Clk1, Clk2, Clk3, Clk4 has a phase shift with respect to the others. Clock signals Clk1, Clk2 control the connection between the inputs $V_{1a}$, $V_{2a}$ and the input capacitors $C_1,C_2$, and the connection between the pairs of feedback capacitors $C_3,C_5$ and $C_4,C_6$ and the inputs of the amplifier $V_{1a'}$, $V_{2a'}$, with a 180° phase-shift. For example, when Clk2 is in the high state and Clk1 is in the low state, input $V_{1a}$ is connected to input capacitor $C_1$, input $V_{2a}$ is connected to input capacitor $C_2$, feedback capacitors $C_3,C_5$ are connected to amplifier input $V_{1a'}$, and feedback capacitors $C_4,C_6$ are connected to amplifier input $V_{2a'}$. Clock signals Clk3, Clk4 control the connection between the input capacitors $C_1,C_2$ and the inputs of the amplifier $V_{1a'}$, $V_{2a'}$, with a 180° phase-shift. For example, when Clk4 is in the high state and Clk3 is in the low state, input capacitors $C_1$, $C_2$ are connected to amplifier inputs $V_{1a'}$, $V_{2a'}$, respectively. Moreover, the clock signals Clk3, Clk4 are phase-shifted with respect to the clock signals Clk1, Clk2. FIG. 6 indicates the connectivity for each circuit switch node, each node labelled according to the clock phases $\varphi_1$, $\varphi_2$, $\varphi_{1a}$, $\varphi_{2a}$ of each corresponding clock signals Clk1, Clk2, Clk3, Clk4.

Figure 7:
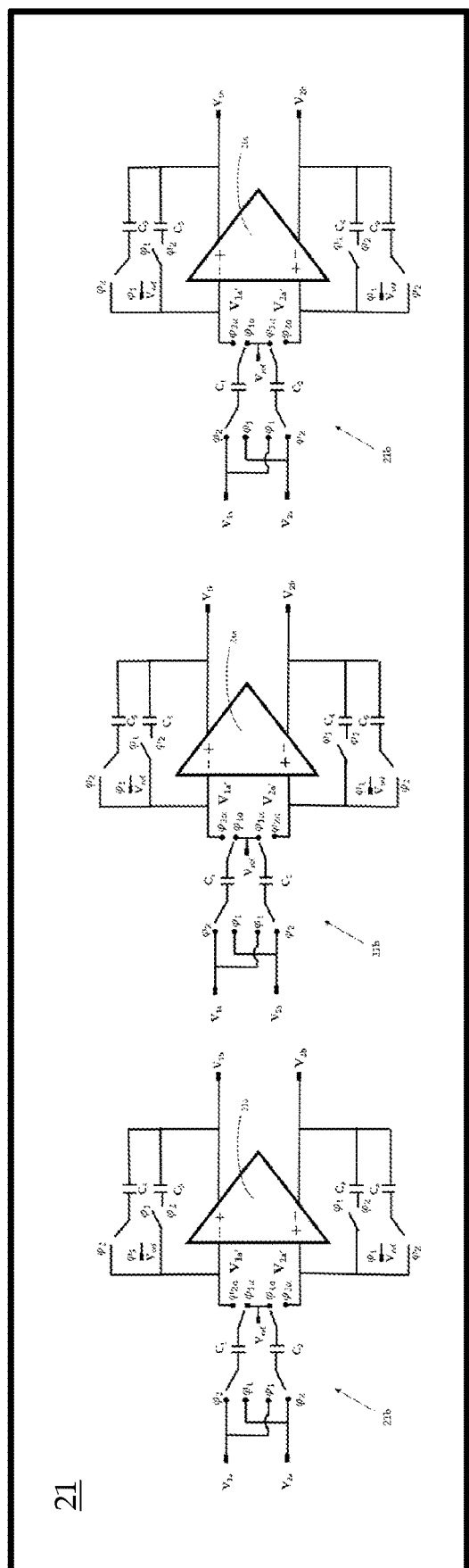
FIG. 7 is a schematic view of a pre-filter stage of the front-end block of the acquisition module of FIGS. 2a and 2b.

As shown in FIG. 7, the pre-filter stage 21 is, preferably, implemented as a third order fully-differential switched capacitor low-pass filter, e.g. using the building units of FIG. 6. More preferably, the pre-filter stage 21 is implemented as third order Cauer (e.g., elliptic) filter with a sampling rates of 256 kHz, a −3 dB bandwidth of 3 kHz.

The pre-filter stage 21 provides amplification while filtering out high-frequency components that can cause aliasing effects (antialiasing pre-filter).

The suppression filter stage 22 performs a suppression of the artifacts by cutting off frequencies above the interested frequency band (2-40 Hz). It is, preferably, implemented as a seventh order fully-differential switched capacitor low-pass filter. More preferably, the suppression filter stage 22 is implemented as elliptic ladder filter operating at 32 kHz and with a cut-off frequency of 40 Hz. Its transfer function is characterized by an attenuation of −52 dB at 130 Hz.

FIGS. 8a-8d are graphs conceptually illustrating the frequency components of a signal at various stages within the front-end block 27. In particular, FIG. 8a illustrates the frequency components of input signal ($V_{1a}$-$V_{2a}$) which comprises both the neural signal 40 located at baseband and the harmonics of the stimulus artifact 41.

FIG. 8b illustrates the frequency components of input signal 40,41 sampled at the first clock frequency $F_{clock\_PreFilter}$ of the pre-filter stage 21. In FIG. 8b, the frequency components of the sampled input signal 42 (generated through sampling at the first clock frequency $F_{clock\_PreFilter}$) are represented at the first clock frequency $F_{clock\_PreFilter}$ only. The frequency components of the 1/f noise 43 are represented superimposed to the neural component 40 of the original input signal at the baseband frequency. FIG. 8b also shows the first cut-off frequency $F_{cut\_PreFilter}$ of the pre-filter stage 21.

The frequency components of the 1/f noise 43 are removed by the pre-filter stage 21 through correlated double sampling, namely through double sampling of the signal such that the second sample—which is the one bearing noise related to itself for stationary reasons—is subtracted from the first sample. In terms of frequency response, this results in a high pass filtering (not represented) that only acts on the 1/f noise 43 but not on the input signal 42.

FIG. 8c illustrates the frequency components downstream from the pre-filter stage 21 (intermediate signal) and sampled at the second clock frequency $F_{clock\_SuppFilter}$ of the suppression filter stage 22. In FIG. 8c, again, the frequency components of the sampled intermediate signal 44 (generated through sampling at the second clock frequency $F_{clock\_SuppFilter}$) are represented at the second clock frequency $F_{clock\_SuppFilter}$ only and the second cut-off frequency $F_{cut\_SuppFilter}$ of the suppression filter stage 22 is also shown. From FIG. 8c, it is clear that the pre-filter 21 attenuates the frequency components of the sampled input signal 42 repeated every multiple of the sample frequency that were located outside of the passband (0 Hz-$F_{cut\_PreFilter}$) of the pre-filter 21 shown in FIG. 8b.

FIG. 8d is a graph that illustrates the frequency components of the output signal ($V_{1out}$-$V_{2out}$) ideally comprising only the neural signal component 40. FIG. 8d shows that the suppression filter 22 attenuates the frequency components from the stimulus artifact 41 and the frequency component of the modulated intermediate signal 44 located outside of the passband (0 Hz-$F_{cut\_SuppFilter}$) of the suppression filter 22 shown in FIG. 8c.

Figures 9A, 9B:
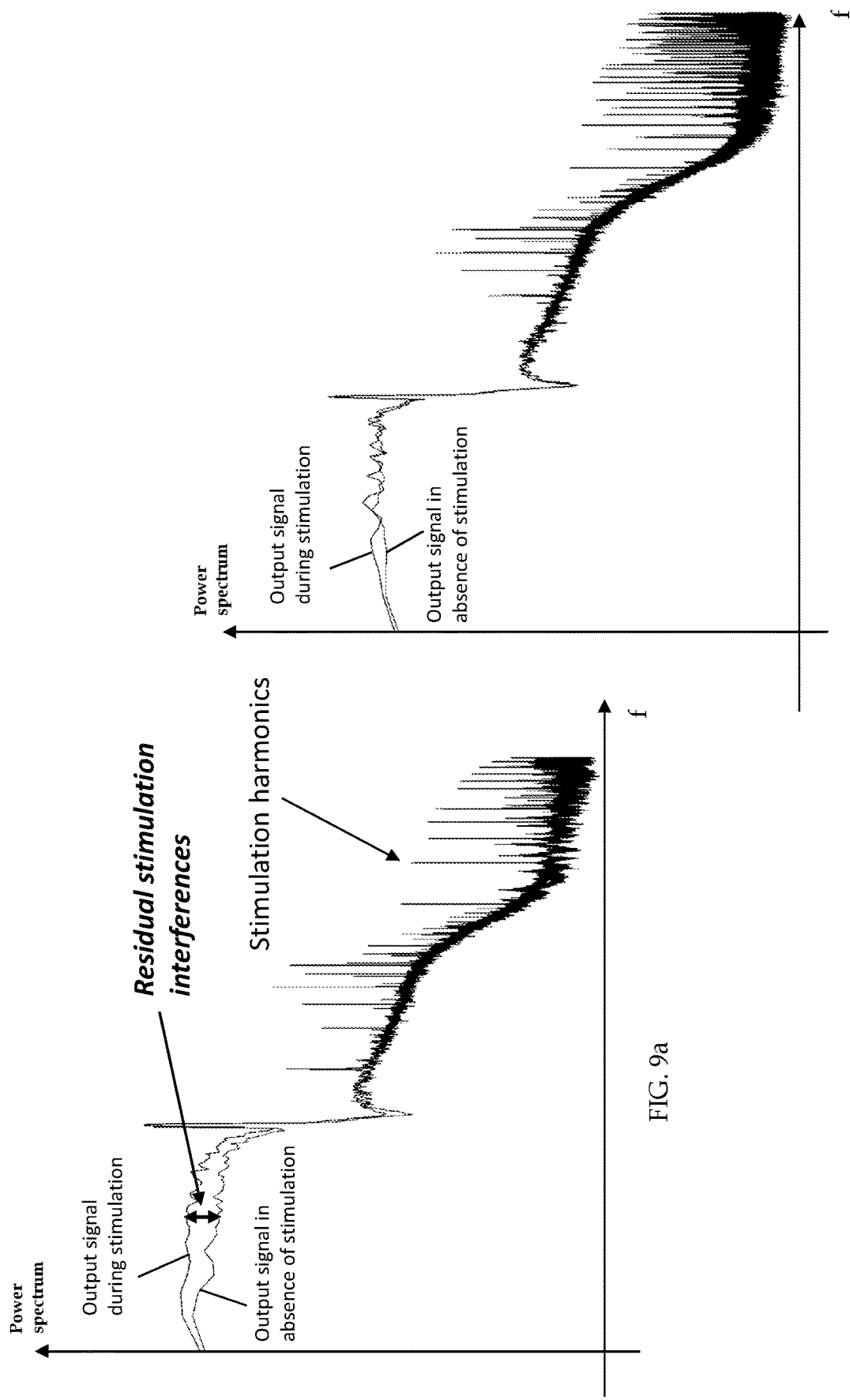
FIGS. 9a and 9b are two logarithmic plots showing the signal power during stimulation and in absence of stimulation, processed using the prior art single-ended analog front end and a fully-differential switched capacitor front end, respectively.

FIG. 9a and FIG. 9b show the effect of the acquisition module 20, namely provided with a multi-stage fully-differential switched capacitor integrated front-end block 21 configured for discrete-time signal processing (FIG. 9b), compared to a prior art single-ended analog front-end (FIG. 9a). In detail, from a comparison of the two figures a relevant reduction of the power mismatch due to residual stimulation interferences appears evident.

The broadband spectral content of the stimulus artifact is theoretically infinite. For any finite sampling rate, this turns into unavoidable aliasing effects which could be reduced by increasing the sampling frequency. However, this would negatively affect the power consumption, which is not acceptable for wearable and/or implantable devices.

Figure 2D:
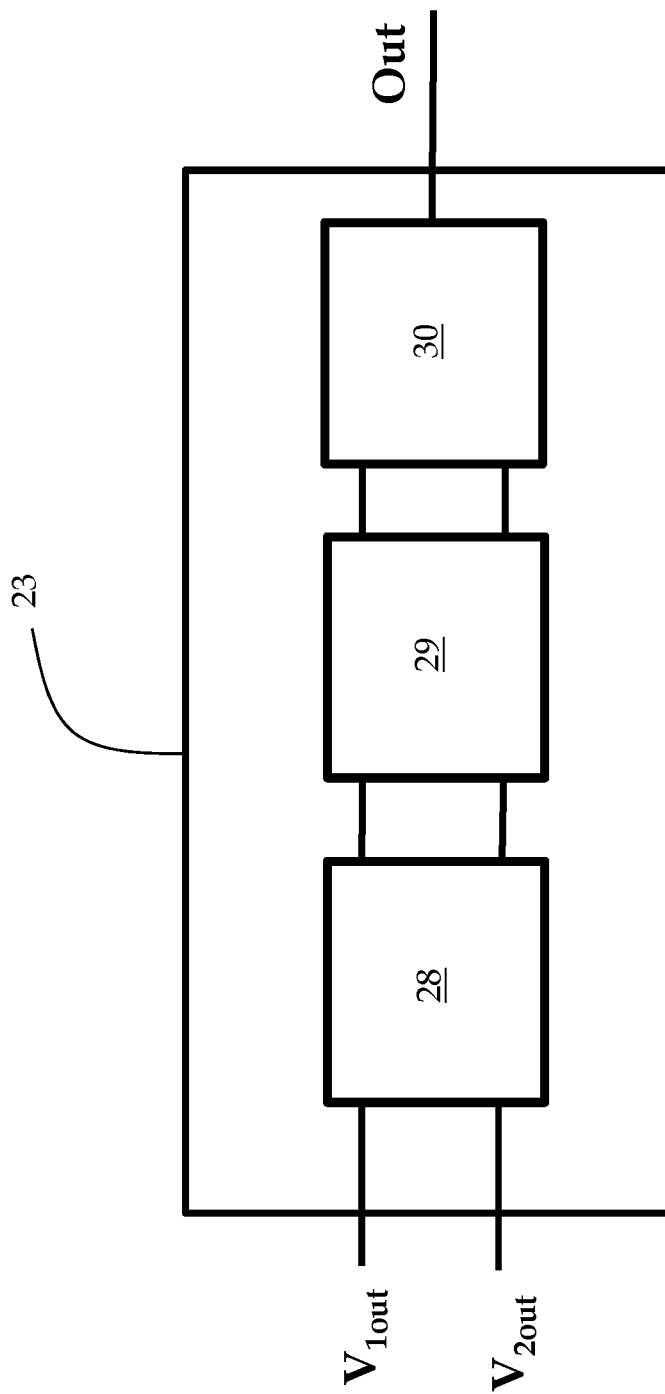

Accordingly, in the A/D converter block 23 a first sampling stage 28 with high sampling rate (preferably at least of 32 kHz) is followed by a filter stage 29 for removing the quantization noise and a decimation stage 30, as shown in FIG. 2d.

The sampling stage 28 comprises a single-bit, third-order, discrete-time delta-sigma (DT-ΔΣ) modulator.

The filter stage 29, being a low-pass filter, is designed to further suppress the residual stimulation interferences, by setting the cut-off frequency at a value smaller than the stimulation frequency.

The first sampling stage 28 of the A/D converter block 23 includes an amplification sub-stage (not illustrated) before the analog-to-digital conversion to adjust the dynamic range of the signal. The A/D converter block 23 has a differential signal as input and provides a digital data at the output.

As shown in FIG. 2b, the acquisition module 20 may optionally comprise an input switch module, a low-pass filter module, and a high-pass filter module 24, 25, 26.

The input switch module 24 may be in communication with the stimulation module 16. For example, the stimulation module 16 may generate and transmit a synchronization signal 24a to the input switch module 24, which may indicate whether to connect the input $V_{1a}$ and $V_{2a}$ to a reference voltage 17 or to leave them disconnected from the recording system during the stimulation. This module 24 provides for a synchronization with the stimulation module 16 or uses the electric stimulus itself in order to be able to disconnect the inputs of the front-end block 27 during stimulus. Disconnecting or grounding the inputs during each stimulus and re-connecting them to the recording system after each stimulation pulse provides for an additional suppression/mitigation of the stimulus artifact, thus unburdening the attenuation requirements at the level of the second suppression filter stage 22.

The opening and closing of the Input Switch module 24 may introduce fluctuations characterized by high frequency frequencies which are removed or mitigated using a second functional module 25 which implements a low-pass filter.

Furthermore, a third functional module 26 provides for high-pass filtering so as to eliminate the DC common mode voltages (before the Input Switch 24) and the DC differential components produced at the interface of the electrode and the brain.

The apparatuses and methods described herein provide a solution for implantable neurostimulator devices requiring for ultra-low power features while being constrained by circuit dimensions.

Implementing a multi-stage (e.g. two stage) front end block using fully-differential switched capacitor integrators configured for discrete-time signal processing (e.g. implementing the correlated double sampling technique) represent a unique solution to record neural signals—namely signal characterized by low amplitudes (<1 µV) at very low frequencies (1-40 Hz)—in presence of the stimulus artifact (usually having an amplitude of tens of mV).

The fully-differential configuration of the front-end block 27 together with the specific design of the basic building units (e.g. the ones of FIG. 3 or of FIG. 6) based on which the pre-filter stage and the suppression filter stage of the front-end block are built, ensures a high CMRR.

Moreover, the basic building units of FIG. 6 which allow the implementation of the correlated double sampling technique permits to achieve a high DC offset and 1/f noise rejection.

Not least, switching capacitors circuits allow for low power and low size implementation.

REFERENCES

Bronstein, J. M. et al. "Deep Brain Stimulation For Parkinson Disease". Archives of Neurology 68.2 (2011):
Burgess, Jonathan G. et al. "Identifying Tremor-Related Characteristics Of Basal Ganglia Nuclei During Movement In The Parkinsonian Patient". Parkinsonism & Related Disorders 16.10 (2010): 671-675.
Chang, Su-Youne et al. "Development Of The Mayo Investigational Neuromodulation Control System: Toward A Closed-Loop Electrochemical Feedback System For Deep Brain Stimulation". Journal of Neurosurgery 119.6 (2013): 1556-1565.
Cogan S F 1. Neural stimulation and recording electrodes. Annu Rev Biomed Eng. 2008; 10:275-309. doi: 10.1146/annurev.bioeng.10.061807.160518.
Eusebio, A. et al. "Deep Brain Stimulation Can Suppress Pathological Synchronisation In Parkinsonian Patients". Journal of Neurology, Neurosurgery & Psychiatry 82.5 (2010): 569-573.
de Hemptinne, C. et al. "Therapeutic Deep Brain Stimulation Reduces Cortical Phase-Amplitude Coupling In Parkinson's Disease". Nature Neuroscience 18.5 (2015): 779-786.
Hamani, Clement et al. "BILATERAL SUBTHALAMIC NUCLEUS STIMULATION FOR PARKINSONS DISEASE". Neurosurgery 62. Supplement 2 (2008): SHC-863 SHC-874.
Kuhn, Andrea A. et al. "Pathological Synchronisation In The Subthalamic Nucleus Of Patients With Parkinson's Disease Relates To Both Bradykinesia And Rigidity". Experimental Neurology 215.2 (2009): 380-387.
Limousin, Patricia et al. "Abnormal Involuntary Movements Induced By Subthalamic Nucleus Stimulation In Parkinsonian Patients". Movement Disorders 11.3 (1996): 231-235.
Moro, E. "Subthalamic Nucleus Stimulation: Improvements In Outcome With Reprogramming". Archives of Neurology 63.9 (2006): 1266-1272.
Priori, A et al. "Rhythm-Specific Pharmacological Modulation Of Subthalamic Activity In Parkinson's Disease". Experimental Neurology 189.2 (2004): 369-379.
Priori, A. et al. "Adaptive Deep Brain Stimulation (Adbs) Controlled By Local Field Potential Oscillations". Experimental Neurology 245 (2013): 77-86.
Qian, X, Chen, Feng Y, Bozhi Ma, et al. A Method for Removal of Deep Brain Stimulation Artifact from Local Field Potentials.
Rosin B, Slovik M, Mitelman R, Rivlin-Etzion M, Haber S, Israel Z, Vaadia E, Bergman H. Closed-Loop Deep Brain Stimulation Is Superior in Ameliorating Parkinsonism. Neuron: Volume 72, Issue 2, 20 Oct. 2011, Pages 370-384.
Santaniello, S et al. "Closed-Loop Control Of Deep Brain Stimulation: A Simulation Study". IEEE Transactions on Neural Systems and Rehabilitation Engineering 19.1 (2011): 15-24.
Stanslaski, S. et al. "Design and validation of a fully implantable, chronic, closed-loop neuromodulation device with concurrent sensing and stimulation". IEEE Trans Neural Syst Rehabil Eng. 20.4 (2011): 410-21.
Yoshida, F. et al. "Value Of Subthalamic Nucleus Local Field Potentials Recordings In Predicting Stimulation Parameters For Deep Brain Stimulation In Parkinson's Disease". Journal of Neurology, Neurosurgery & Psychiatry 81.8 (2010): 885-889.

The invention claimed is:

1. An apparatus comprising:
a stimulation module configured to generate a stimulation signal to be sent to at least one implantable electrode, and
an acquisition module configured to acquire a signal measured by the at least one implantable electrode from a patient,
wherein the acquisition module comprises a front-end block configured to amplify a potential difference of input signals ($V_{1a}$, $V_{2a}$) received by the acquisition module and to filter a stimulus artifact by cutting off frequencies above a predefined frequency band; characterized in that the front-end block comprises a multi-stage fully-differential switched capacitor circuit configured for discrete-time signal processing.

2. The apparatus of claim 1, wherein the front-end block comprises a pre-filter stage and a suppression filter stage positioned downstream from the pre-filter stage.

3. The apparatus of claim 2, wherein each of the pre-filter stage and the suppression filter stage comprising a fully-differential switched capacitor circuit configured for discrete-time signal processing.

4. The apparatus of claim 3, wherein the pre-filter stage comprises a first fully-differential low-pass switched capacitor filter, clocked at a first clock frequency.

5. The apparatus of claim 4, wherein the suppression filter stage comprises a second fully-differential low-pass switched capacitor filter, clocked at a second clock frequency.

6. The apparatus of claim 4, wherein the fully-differential switched capacitor filter of the pre-filter stage and of the suppression filter stage comprises at least one bilinear switched capacitor integrator.

7. The apparatus of claim 6, wherein the at least one bilinear switched capacitor integrator is configured to implement correlated double sampling.

8. The apparatus of claim 6, wherein the at least one bilinear switched capacitor integrator comprises two inputs ($V_{1a}, V_{2a}$) which are alternatively connectable to one end of two input capacitors ($C_1, C_2$), the other end of the two input capacitors ($C_1, C_2$) being configured to alternatively connect to a reference voltage source ($V_{ref}$) or, each respectively, to one of two inputs of an operational amplifier.

9. The apparatus of claim 8, wherein each input of the operational amplifier being connectable to one respective output of the operational amplifier through interposition of a first ($C_3, C_5$) and a second ($C_4, C_6$) pair of feedback capacitors, respectively.

10. The apparatus of claim 9, wherein the feedback capacitor pairs ($C_3, C_5$) and ($C_4, C_6$,) comprise each a first ($C_3, C_4$) and a second ($C_5, C_6$) feedback capacitors connected in parallel, and are configured to alternatively connect to the respective input of the operational amplifier.

11. The apparatus of claim 6, wherein the at least one bilinear switched capacitor integrator comprises two inputs ($V_{1a}, V_{2a}$) which are alternatively connectable to one end of two input capacitors ($C_1, C_2$), the other end of the two input capacitors ($C_1, C_2$) being configured to alternatively connect to a reference voltage source ($V_{ref}$) or, each respectively, to one of two inputs of an operational amplifier, each input of the operational amplifier being connectable to one respective output of the operational amplifier through interposition of a first ($C_3$) and a second ($C_4$) feedback capacitor, respectively.

12. The apparatus of claim 3, wherein the fully-differential switched capacitor circuit of the pre-filter stage and/or of the suppression filter stage is implemented as ladder filter comprising a plurality of switched capacitor integrators in an active emulation of lossless LC ladder structure.

13. The apparatus of claim 5, wherein the first fully-differential switched capacitor filter of the pre-filter stage has an order lower than an order of the second fully-differential switched capacitor filter of the suppression filter stage.

14. The apparatus of claim 5, wherein the first clock frequency of the first fully-differential switched capacitor filter of the pre-filter stage is greater than the second clock frequency of the second fully-differential switched capacitor filter of the suppression filter stage.

15. The apparatus of claim 4, wherein the first clock frequency is at least 1 KHz.

16. The apparatus of claim 5, wherein a first cut-off frequency of the first fully-differential switched capacitor filter of the pre-filter stage is greater than a second cut-off frequency of the second fully-differential switched capacitor filter of the suppression filter stage.

17. The apparatus of claim 5, wherein a first cut-off frequency of the first fully-differential switched capacitor filter of the pre-filter stage is at least 50 Hz and is lower than the second clock frequency.

18. The apparatus of claim 5, wherein a second cut-off frequency of the second fully-differential switched capacitor filter of the suppression filter stage is in the range of about 35-2000 Hz.

19. The apparatus of claim 1, wherein the acquisition module further comprises an A/D converter block connected downstream from the front-end block.

20. The apparatus of claim 19, wherein the A/D converter block optionally comprises a delta-sigma converter.

21. The apparatus of claim 19, wherein the A/D converter block comprises a fully-differential switched-capacitor circuit.

22. The apparatus of claim 19, wherein the A/D converter block comprises a first sampling stage, followed by a filter stage configured for removing a quantization noise and a decimation stage.

23. The apparatus of claim 1, wherein the acquisition module further comprises at least one functional module between:
a first functional module configured for receiving an input synchronization signal coming from the stimulation module for disconnecting or grounding the inputs of the front-end block during stimulus pulses generated by the stimulation module, the first functional module being connected upstream from the front-end block; and/or
a second functional module configured for eliminating high frequencies in a signal produced by the operation of the first functional module; and/or
a third functional module configured for providing high-pass filtering so as to mitigate offset potentials at the at least one implantable electrode.

24. A method comprising:
receiving a signal using at least one implantable electrode;
amplifying and pre-filtering the signal acquired by using a first stage comprising a fully-differential switched capacitor circuit configured for discrete-time signal processing; and
filtering the amplified and pre-filtered signal by cutting off frequencies above a predefined frequency band using a second stage comprising a fully-differential switched capacitor circuit configured for discrete-time signal processing.

25. The method of claim 24, wherein amplifying the signal or filtering the amplified signal comprises correlated double sampling.

26. The method of claim 24, wherein amplifying the signal is performed using a first fully-differential switched capacitor filter, clocked at a first clock frequency.

27. The method of claim 26, wherein the step of filtering the amplified signal is performed using a second fully-differential switched capacitor filter, clocked at a second clock frequency.

28. The method of claim 27, wherein the first clock frequency is greater than the second clock frequency.

29. The method of claim 27, wherein a first clock signal at the first clock frequency and/or a second clock signal at the second clock frequency are configured to time an alternative connection and disconnection of second feedback capacitors ($C_5,C_6$) of feedback capacitor pairs ($C_3,C_5$) and ($C_4,C_6$) to the input of an operational amplifier.

30. The method of claim 27, wherein the first fully-differential switched capacitor filter is a low-pass filter with a first cut-off frequency and the second fully-differential switched capacitor filter is a low-pass filter with a second cut-off frequency smaller than the first cut-off frequency.

31. The method of claim 27, wherein the first fully-differential switched capacitor filter of the pre-filter stage has an order lower than an order of the second fully-differential switched capacitor filter of the suppression filter stage.

32. The method of claim 25, wherein the correlated double sampling is implemented using a bilinear switched capacitor integrator, and wherein the bilinear switched capacitor integrator comprises two inputs ($V_{1a},V_{2a}$) which are alternatively connectable to one end of two input capacitors ($C_1, C_2$), another end of the two input capacitors ($C_1, C_2$) being configured to alternatively connect to a reference voltage source ($V_{ref}$) or, each respectively, to one of two inputs of an operational amplifier.

33. The method of claim 32, wherein each input of the operational amplifier being connectable to one respective output of the operational amplifier through interposition of a first pair ($C_3,C_5$) and a second pair ($C_4,C_6$) of feedback capacitors, respectively.

34. The method of claim 33, wherein the first pair ($C_3,C_5$) and the second pair ($C_4,C_6$) of feedback capacitors comprise each a first ($C_3,C_4$) and a second ($C_5,C_6$) feedback capacitors connected in parallel, and are configured to alternatively connect to the respective input of the operational amplifier.

* * * * *